(12) United States Patent
Han

(10) Patent No.: US 11,234,654 B2
(45) Date of Patent: Feb. 1, 2022

(54) PSEUDO-CT GENERATION FROM MR DATA USING A FEATURE REGRESSION MODEL

(71) Applicant: Elekta, Inc., Atlanta, GA (US)

(72) Inventor: Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 451 days.

(21) Appl. No.: 16/354,495

(22) Filed: Mar. 15, 2019

(65) Prior Publication Data

US 2019/0209099 A1 Jul. 11, 2019

Related U.S. Application Data

(63) Continuation of application No. 14/881,903, filed on Oct. 13, 2015, now Pat. No. 10,307,108.

(51) Int. Cl.
*A61B 5/00* (2006.01)
*G01R 33/56* (2006.01)
(Continued)

(52) U.S. Cl.
CPC .......... *A61B 5/7267* (2013.01); *A61B 5/0035* (2013.01); *A61B 5/055* (2013.01);
(Continued)

(58) Field of Classification Search
CPC ..... A61B 5/7267; A61B 5/0035; A61B 5/055; A61B 5/7278; A61B 2090/3762;
(Continued)

(56) References Cited

U.S. PATENT DOCUMENTS

| 10,307,108 B2 | 6/2019 | Han |
| 2011/0172514 A1 | 7/2011 | Lee et al. |

(Continued)

FOREIGN PATENT DOCUMENTS

| AU | 2016338923 A1 | 4/2018 |
| CN | 1595451 A | 3/2005 |

(Continued)

OTHER PUBLICATIONS

"European Application Serial No. 16790780.7, Response filed Nov. 18, 2019 to Communication Pursuant to Article 94(3) EPC dated Jul. 18, 2019", 18 pgs.

(Continued)

*Primary Examiner* — Hien N Nguyen
(74) *Attorney, Agent, or Firm* — Schwegman Lundberg & Woessner, P.A.; Sanjay Agrawal

(57) ABSTRACT

Systems and methods are provided for generating a pseudo-CT prediction model that can be used to generate pseudo-CT images. An exemplary system may include a processor configured to retrieve training data including at least one MR image and at least one CT image for each of a plurality of training subjects. For each training subject, the processor may extract a plurality of features from each image point of the at least one MR image, create a feature vector for each image point based on the extracted features, and extract a CT value from each image point of the at least one CT image. The processor may also generate the pseudo-CT prediction model based on the feature vectors and the CT values of the plurality of training subjects.

20 Claims, 14 Drawing Sheets

(51) Int. Cl.
| | |
|---|---|
| *G06T 5/00* | (2006.01) |
| *G06T 11/00* | (2006.01) |
| *G16H 30/40* | (2018.01) |
| *G16H 30/20* | (2018.01) |
| *G16H 50/50* | (2018.01) |
| *A61B 5/055* | (2006.01) |
| *A61N 5/10* | (2006.01) |
| *A61B 90/00* | (2016.01) |

(52) U.S. Cl.
CPC .......... *A61B 5/7278* (2013.01); *A61N 5/1039* (2013.01); *G01R 33/5608* (2013.01); *G06T 5/007* (2013.01); *G06T 11/008* (2013.01); *G16H 30/20* (2018.01); *G16H 30/40* (2018.01); *G16H 50/50* (2018.01); *A61B 2090/3762* (2016.02); *A61B 2576/00* (2013.01); *G06T 2207/10081* (2013.01); *G06T 2207/10088* (2013.01); *G06T 2207/20081* (2013.01)

(58) Field of Classification Search
CPC .... A61B 2576/00; G16H 30/40; G16H 30/20; G16H 50/50; G01R 33/5608; G06T 5/007; G06T 11/008; G06T 2207/10081; G06T 2207/10088; G06T 2207/20081; A61N 5/1039
See application file for complete search history.

(56) References Cited

U.S. PATENT DOCUMENTS

| | | | |
|---|---|---|---|
| 2011/0286649 | A1 | 11/2011 | Reisman et al. |
| 2011/0302118 | A1 | 12/2011 | Melvin et al. |
| 2014/0212013 | A1 | 7/2014 | Han |
| 2017/0100078 | A1 | 4/2017 | Han |

FOREIGN PATENT DOCUMENTS

| | | |
|---|---|---|
| CN | 101061490 A | 10/2007 |
| CN | 101732048 A | 6/2010 |
| CN | 104039262 A | 9/2014 |
| CN | 108770373 A | 11/2018 |
| CN | 110636772 | 12/2019 |
| EP | 3362984 A1 | 8/2018 |
| JP | 2016504167 | 2/2016 |
| JP | 2019536526 | 12/2019 |
| RU | 2452385 | 6/2012 |
| RU | 2550542 | 5/2015 |
| WO | WO-2017066247 A1 | 4/2017 |

OTHER PUBLICATIONS

"European Application Serial No. 16790780.7, Communication Pursuant to Article 94(3) EPC dated Dec. 20, 2019", 4 pgs.
"U.S. Appl. No. 14/881,903, Examiner Interview Summary dated Aug. 27, 2018", 2 pgs.
"U.S. Appl. No. 14/881,903, Examiner Interview Summary dated Nov. 20, 2018", 3 pgs.
"U.S. Appl. No. 14/881,903, Final Office Action dated Oct. 22, 2018", 8 pgs.
"U.S. Appl. No. 14/881,903, Non Final Office Action dated May 18, 2018", 16 pgs.
"U.S. Appl. No. 14/881,903, Notice of Allowability dated Jan. 30, 2019", 4 pgs.
"U.S. Appl. No. 14/881,903, Notice of Allowance dated Jan. 18, 2019", 14 pgs.
"U.S. Appl. No. 14/881,903, Response filed Aug. 20, 2018 to Non Final Office Action dated May 18, 2018", 13 pgs.
"U.S. Appl. No. 14/881,903, Response filed Nov. 27, 2018 to Final Office Action dated Oct. 22, 2018", 11 pgs.
"European Application Serial No. 16790780.7, Response filed Dec. 5, 2018 to Office Action dated May 28, 2018", 72 pgs.
"International Application Serial No. PCT/US2016/056538, International Preliminary Report on Patentability dated Apr. 26, 2018", 8 pgs.
"International Application Serial No. PCT/US2016/056538, International Search Report dated Feb. 9, 2017", 4 pgs.
"International Application Serial No. PCT/US2016/056538, Written Opinion dated Feb. 9, 2017", 6 pgs.
Hofmann, Matthias, et al., "MRI-Based Attenuation Correction for PET/MRI: A Novel Approach Combining Pattern Recognition and Atlas Registration", The Journal of Nuclear Medicine, Society of Nuclear Medicine, US, vol. 49, No. 11, (Nov. 1, 2008), 1875-1883.
"U.S. Appl. No. 14/881,903, 312 Amendment filed May 1, 2019", 3 pgs.
"U.S. Appl. No. 14/881,903, PTO Response to Rule 312 Communication dated May 6, 2019", 2 pgs.
"European Application Serial No. 16790780.7, Communication Pursuant to Article 94(3) EPC dated Jul. 18, 2019", 4 pgs.
"U.S. Appl. No. 15/921,222, Response filed Dec. 27, 2019 to Restriction Requirement dated Aug. 14, 2019", 10 pgs.
"U.S. Appl. No. 15/458,824, Final Office Action dated Feb. 18, 2020", 26 pgs.
"Japanese Application Serial No. 2019-550635, Voluntary Amendment filed Nov. 12, 2019", w English claims, 5 pgs.
"European Application Serial No. 17865224.4, Response to Communication Pursuant to Rules 161 and 162 filed Dec. 10, 2019", 10 pgs.
"European Application Serial No. 16790780.7, Response filed Jan. 28, 2020 to Communication Pursuant to Article 94(3) EPC dated Dec. 20, 2019", 3 pgs.
"European Application Serial No. 16790780.7, Communication Pursuant to Article 94(3) EPC dated Jun. 1, 2021", 4 pgs.
"European Application Serial No. 16790780.7, Response filed Jul. 9, 2021 to Communication Pursuant to Article 94(3) EPC dated Jun. 1, 2021", 20 pgs.
"Chinese Application Serial No. 201680072831.7, Office Action dated Nov. 1, 2021", w/ English translation, 13 pgs.
Zhang, Bo, et al., "Establishment of CT Imaging Accessory Diagnostic Model Based on Artificial Neural Network in Hepatocellular Carcinoma", J Pract Radiol, No. 9, (Sep. 25, 2006).

PSEUDO-CT GENERATION FROM MR DATA USING A FEATURE REGRESSION MODEL

CROSS-REFERENCE TO RELATED APPLICATION

The present application is a continuation of U.S. application Ser. No. 14/881,903, filed Oct. 13, 2015, which is related to U.S. application Ser. No. 14/881,939, filed Oct. 13, 2015, and titled "Pseudo-CT Generation from MR Data Using Tissue Parameter Estimation," the entire contents of each of which are incorporated herein by reference in their entireties.

TECHNICAL FIELD

This disclosure generally relates to radiation therapy or radiotherapy. More specifically, the disclosure relates to systems and methods for generating pseudo-CT images from MR data for use in developing a radiation therapy treatment plan to be used during radiotherapy.

BACKGROUND

Radiotherapy is used to treat cancers and other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine.

Traditionally, for each patient, a radiation therapy treatment plan ("treatment plan") may be created using an optimization technique based on clinical and dosimetric objectives and constraints (e.g., the maximum, minimum, and mean doses of radiation to the tumor and critical organs). The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Computed Tomography (CT) imaging traditionally serves as the primary source of image data for treatment planning for radiation therapy. CT images offer accurate representation of patient geometry, and CT values can be directly converted to electron densities (e.g., Hounsfield units) for radiation dose calculation. However, using CT causes the patient to be exposed to additional radiation dosage. In addition to CT images, magnetic resonance imaging (MRI) scans can be used in radiation therapy due to their superior soft-tissue contrast, as compared to CT images. MRI is free of ionizing radiation and can be used to capture functional information of the human body, such as tissue metabolism and functionality.

Thus, MRI can be used to complement CT for more accurate structure contouring. However, MRI intensity values are not directly related to electron densities and cannot be directly used for dose computation; therefore, it is desirable to convert a MR image into a corresponding derived image, usually a CT image (often referred to as a "pseudo-CT image"). A pseudo-CT image, like a real CT image, has a set of data points that indicate CT values that are directly convertible to electron densities for radiation dose calculation. Thus, a pseudo-CT image derived from an MR image can be used to facilitate patient dose computation in radiation therapy treatment planning. Therefore, it is desirable to accurately generating a pseudo-CT image using MR image data in order for patients to be spared from additional radiation exposure arising from CT imaging. What is needed is for pseudo-CT images to be able to replace "real" CT images.

Typically, to create pseudo-CT images, atlas images are employed. An atlas image is a pre-existing image that is used as a reference to facilitate how a new image is to be translated to generate a derived image. For example, in the pseudo-CT image generation context, an atlas MR image and an atlas CT image can be used as references for generating a derived CT image from a new MR image. Atlas images can be previously generated of the same region of interest for the same patient who is the subject of the new MR images, where these atlas images have been analyzed to identify structures of interest. For example, in many treatment or diagnostic situations, the patient will need to be subjected to imaging at different times over the course of treatment or diagnosis. However, this need not always be true, for example, the atlas images do not need to be images of the same person.

The atlas MR image and the atlas CT image are preferably aligned with each other via a registration technique (i.e., such that an atlas MR image and an atlas CT image are "registered" with each other, or are in "registration"). With such registration, a give point in the atlas MR image for a particular location of the subject can be mapped to a given point in the atlas CT image for the same particular location (and vice versa). However, there may be a certain amount of error that can be present in this registration. As such, the registration between the atlas MR and the atlas CT may not be perfect.

In order to replace a real CT image, the pseudo-CT image should be as close as possible to a real CT image of the patient for the purpose of dose computation in radiation therapy treatment planning or for generating digitally reconstructed radiographs (DRRs) for image guidance. However, there is not a simple mathematical relationship between CT image intensity values (CT values) and MR intensity values. The difficulty arises because MR intensity values are not standardized and can vary significantly depending upon different MR scanner settings or different MR imaging sequence parameters. Thus, existing techniques, such as assigning CT values based on tissue segmentation of an MR image or those based on point comparison and weighted combination, provide only a very rough assignment, resulting in existing pseudo-CT images that lack the anatomical details of a true CT image.

Therefore, there is a need for generating pseudo-CT images with improved quality that are capable of replacing real CT images for the purposes of dose computation in treatment planning, generating digitally reconstructed radiographs (DRRs) for image guidance, and the like.

SUMMARY

In one aspect, the present disclosure involves a system for generating a pseudo-CT prediction model. The system may include a database configured to store training data comprising MR data and CT data of a plurality of training subjects. Each training subject may have at least one MR image and at least one CT image. The system may also include a processor communicatively coupled to the database for accessing information stored in the database. The system may further include a memory communicatively coupled to the processor. The memory may store instructions that, when executed by the processor, configures the processor to perform various operations. The operations may include accessing the database to retrieve the training data including at least one MR image and at least one CT image for each of the plurality of training subjects. For each training subject, the operations may include extracting a plurality of features from each image point of the at least one MR image, creating a feature vector for each image point based on the extracted features, and extracting a CT value from each image point of the at least one CT image. The operations may also include generating the pseudo-CT prediction model based on the feature vectors and the CT values of the plurality of training subjects.

In another aspect, the present disclosure involves a system for generating a pseudo-CT image. The system may include a processor and a memory communicatively coupled to the processor. The memory may store instructions that, when executed by the processor, configures the processor to perform various operations. The operations may include receiving an MR image of a patient and extracting a plurality of features from each image point of the MR image. The operations may also include creating a feature vector for each image point based on the extracted features. The operations may further include determine a CT value for each image point based on the feature vector created for that image point using a predictive model. In addition, the operations may include generating the pseudo-CT image based on the CT values determined for all image points.

In a further aspect, the present disclosure involves a system for generating a pseudo-CT prediction image for a patient. The system may include a processor and a memory communicatively coupled to the processor. The memory may store instructions that, when executed by the processor, configures the processor to perform various operations. The operations may include receiving an MR image of the patient and extracting a plurality of features from the MR image. The operations may also include generating an intermediate image using a predictive model based on the extracted features. The operations may further include extracting one or more features from the intermediate image. In addition, the operations may include generating the pseudo-CT image for the patient based on the plurality of features extracted from the MR image and the one or more features extracted from the intermediate image.

In a further aspect, the present disclosure involves a system for generating a pseudo-CT prediction model. The system may include a database configured to store training data comprising multi-channel MR data and CT data of a plurality of training subjects. Each training subject may have multiple MR images and at least one CT image. The system may also include a processor communicatively coupled to the database for accessing information stored in the database. The system may further include a memory communicatively coupled to the processor. The memory may store instructions that, when executed by the processor, configures the processor to perform various operations. The operations may include accessing the database to retrieve the training data including multiple MR images and at least one CT image for each of the plurality of training subjects. For each training subject, the operations may include determining at least one tissue parameter map based on the multiple MR images and obtaining CT values based on the at least one CT image. The operations may also include generating the pseudo-CT prediction model based on the tissue parameter maps and the CT values of the plurality of training subjects.

In a further aspect, the present disclosure involves a system for generating a pseudo-CT image. The system may include a processor and a memory communicatively coupled to the processor. The memory may store instructions that, when executed by the processor, configures the processor to perform various operations. The operations may include receiving multiple multi-channel MR images of a patient and converting the multiple multi-channel MR images into at least one tissue parameter map. The operations may also include generating CT values by applying a predictive model to the at least one tissue parameter map. The operations may further include generating the pseudo-CT image based on the CT values generated by the predictive model.

In a further aspect, the present disclosure involves a computer-implemented method for generating a pseudo-CT prediction model. The method may include retrieving training data including multiple multi-channel MR images and at least one CT image for each of a plurality of training subjects. For each training subject, the method may include determining at least one tissue parameter map based on the multiple multi-channel MR images and obtaining CT values based on the at least one CT image. The method may also include generating the pseudo-CT prediction model based on the tissue parameter maps and the CT values of the plurality of training subjects.

It is to be understood that both the foregoing general description and the following detailed description are exemplary and explanatory only and are not restrictive of the disclosed embodiments, as claimed. These and other features and advantages of the present disclosure will be apparent to those having ordinary skill in the art upon review of the teachings as described in the following description, drawings and claims.

BRIEF DESCRIPTION OF THE DRAWINGS

The accompanying drawings, which are incorporated in and constitute a part of this specification, illustrate disclosed embodiments and, together with the description and claims, serve to explain the disclosed embodiments. Such embodiments are demonstrative and not intended to be exhaustive or exclusive embodiments of the present apparatuses, systems, or methods. In the drawings, which are not necessarily drawn to scale, like numerals may describe similar components in different views. Like numerals having letter suffixes or different letter suffixes may represent different instances of similar components.

DETAILED DESCRIPTION

Reference will now be made in detail to the disclosed embodiments, examples of which are illustrated in the accompanying drawings. Wherever convenient, the same reference numbers will be used throughout the drawings to refer to the same or like parts.

In one embodiment, in order to create a pseudo-CT image (also referred to as a synthetic CT image or a derived CT image) from an MR image, a learning-based approach that includes a training module and a prediction module is provided. The training module constructs a predictive model (also referred to as a regression model) that can be used to predict a CT value for any given voxel based on features extracted from one or more MR images for a selected location. During training, MR scans and CT scans are collected from a plurality of existing patients to form training data. The training data include pairs of pre-aligned CT and MR images from existing patients. For each pair of images, the corresponding MR and CT values are known and in registration for every pixel or voxel (also referred to as an image point that includes both 2D and 3D scenarios).

The predictive model can be trained using the training data. During the training phase, regression methods (e.g., statistical learning, regression analysis, or machine learning techniques) can be used on the collected training data to train the model. After the predictive model is trained, the model can be used by the prediction module to predict the CT value for each image point of a patient image. Therefore, the trained model can be used to create pseudo-CT images from MR data of any future scans, and for the same or a different patent.

Figure 1:
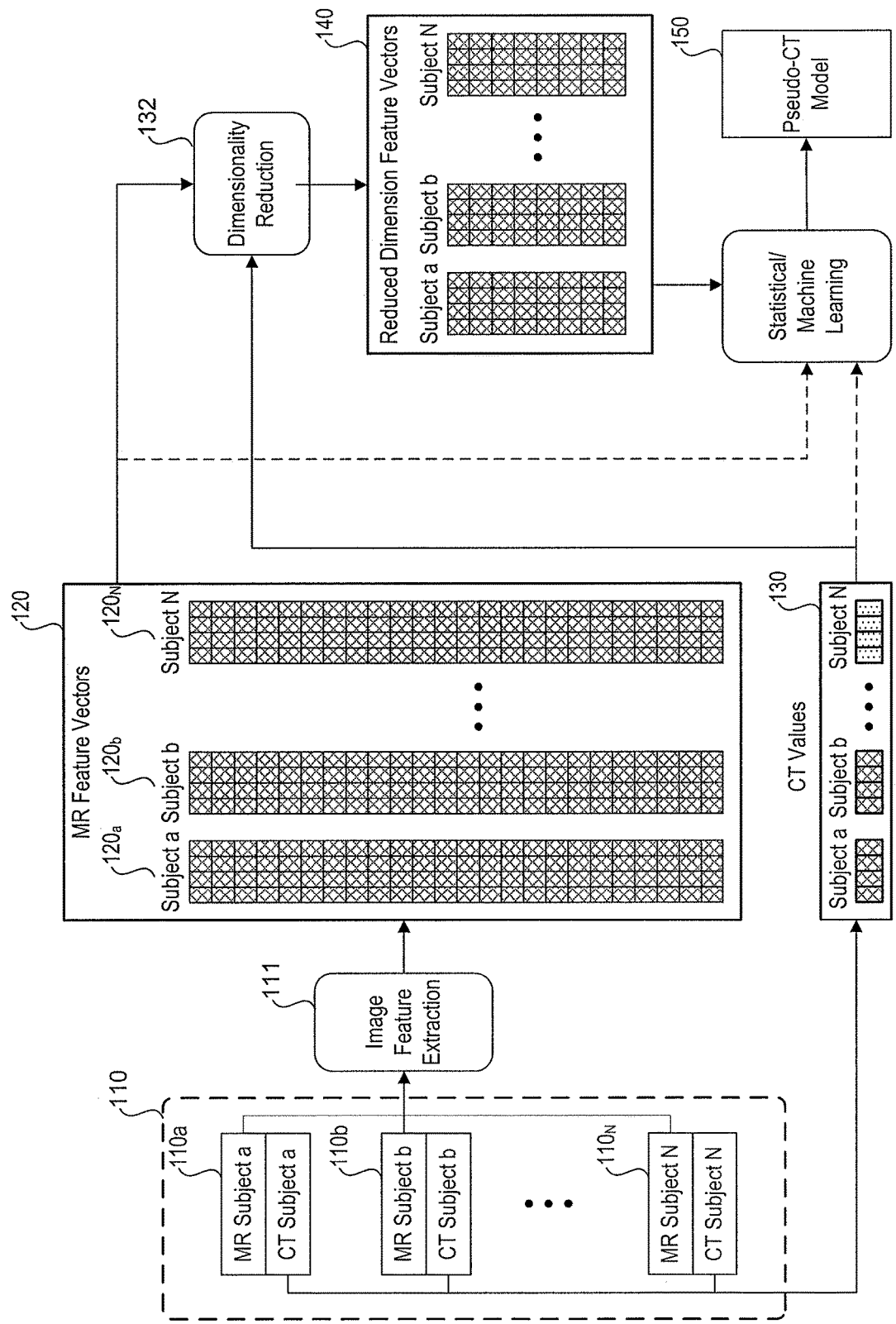
FIG. 1 is a diagram of an exemplary process for building a pseudo-CT predictive model.

FIG. 1 illustrates a flowchart of an exemplary process for building a pseudo-CT predictive model 150, consistent with the disclosed embodiments. As illustrated, one embodiment is a learning-based approach that includes a training module and a prediction module. The training module creates, in an embodiment, a regression model (e.g., pseudo-CT model 150) that can be used by the prediction module to predict pseudo-CT values based on one or more new MR scans.

In one embodiment, training data 110 may be collected from existing patients or subjects (collectively referred to as "training subjects"). The training subjects may have both MR scans and corresponding CT scans previously taken and available to be used to build the pseudo-CT predictive model 150. Training data 110 may include data for a plurality of training subjects who have had at least one MR scan and at least one CT scan (e.g., training subject data 110a-110$_N$). The greater number of training subjects to provide the training data (e.g., the larger the data set) will typically allow for a better pseudo-CT prediction model to be generated compared to a model made of a smaller set of data. Training subject data 110a-110$_N$ includes pairs of pre-aligned MR and CT images. The MR and CT images may be acquired separately; therefore if the images are overlaid upon one another, they typically do not match. So, image registration, as known in the art, is used to pre-align the MR and CT images. According to some embodiments, the MR scans associated with the training subjects may be generated by the same MR scanner as that of MR scan(s) of a new patient for which a pseudo-CT image is desired. In other embodiments, the MR scans associated with the training subjects may be generated by different MR scanners. Further, multiple MR scans associated with a single training subject may include MR scans of different contrast properties (e.g., T1-weighted, T2-weighted, etc.), to provide more accurate pseudo-CT generation results.

An image feature extraction module 111 may be used to extract image features from the MR images associated with the training data 110. Image features may refer to numerical (e.g., intensity values, coordinate locations of the feature and the like) or categorical properties (e.g., a tissue type, a structure label and the like) of an MR voxel. For example, an "intensity feature" may refer to the intensity value of an MR voxel. However, any single MR feature may not be enough to adequately represent the MR voxels for the purposes of generating pseudo-CT images. For example, the intensity value of an MR voxel taken alone provides an ambiguous representation for CT estimation. A single intensity value is ambiguous because, among other things, two MR voxels of the same intensity level can belong to different tissues (e.g., bone and air) having different CT values. As used herein, the term "tissue" refers to a classification and is not merely to suggest specific types of tissue; e.g., air is not a tissue. Thus, a plurality of feature types for each MR voxel of an MR scan are extracted in order to provide a more distinctive description of the MR voxels.

With multiple MR images or multi-channel MR images, a rich set of image-based features can be extracted, which provides more information and can lead to more accurate pseudo-CT prediction. Image feature extraction module 111 can be used to extract features from each image or each channel separately (e.g., MR feature vectors 120).

The resulting MR feature vectors 120 may include a plurality sets of collected image feature vectors, each associated with a training subject's MR scan(s) (e.g., image vector sets 120a-120$_N$). Each image feature vector set 120a-120$_N$ may include a plurality of feature vectors. For example, each column of a given feature vector set (e.g., 120a) may represent a feature vector, which includes a plurality of features as vector elements. The plurality of features of a feature vector represent different types of image features associated with, for example, an image point (e.g., a voxel) of an MR scan/image for a training subject. The number of the feature elements in a feature vector (e.g., the number of elements in a column) is also referred to the dimension of the feature vector. In some embodiments, feature vectors may also be arranged in rows or other suitable forms. Feature extraction according to disclosed embodiments is discussed in additional detail below with respect to FIG. 2.

Figure 2:
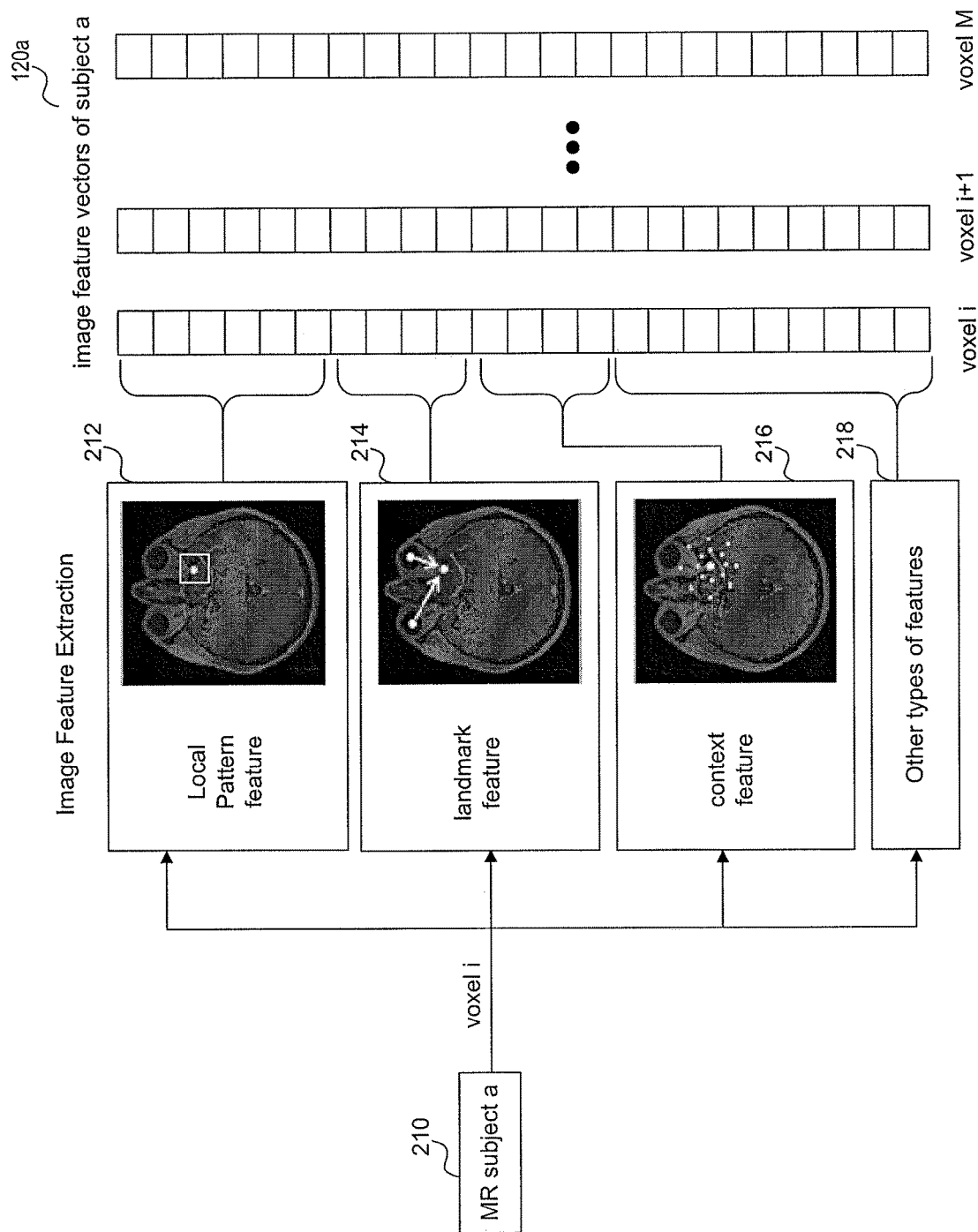
FIG. 2 is a diagram of an exemplary process for extracting features from each voxel of an MR image.

FIG. 2 illustrates a feature extraction process consistent with the disclosed embodiments. A plurality of image features may be extracted for each MR voxel of an MR scan for a patient (e.g., MR subject a 210). As shown in FIG. 2, the extracted image features may include a local pattern feature 212, a landmark feature 214, a context feature 216, and various other types of features 218. Each of these features may be represented by one or more feature elements, shown as small blocks collectively forming a feature vector column in FIG. 2. The features can be associated with an image pixel (in 2D), an image voxel (in 3D), or a collection of image points (e.g., an image patch, in 2D or 3D). For example, FIG. 2 shows feature vectors (e.g., columns) associated with voxel i, voxel i+1, . . . , voxel M. A plurality of feature vectors, for example, a collection of feature vectors associated with multiple voxels of an MR image (e.g., voxels i to M), may form the feature vector set 120a corresponding to training subject a.

A non-limiting list of potential image features includes:
Intensity features: MR image intensity values at multiple scales—either the raw intensity values or after some pre-processing, such as MR intensity bias correction and/or MR intensity standardization/normalization;
Landmark-based features: the relative location, distance or other geometric features that are computed for a given voxel with respect to one or more landmark points (e.g., Anterior commissure-posterior commissure (AC-PC) points of the brain, center of each eye ball, and the like);
Context features: any other image features that are computed at certain neighborhood locations of the given point;
Location features: the normalized coordinates of each voxel. The normalization may be accomplished, for example, by aligning each image to a common reference frame using either linear or non-linear image registration;
Patch features: a patch may refer in some embodiments to a sub-region or a sub-set of an image surrounding the image voxel for which the features are computed. For example, a patch may include 5×5×5 voxels in size, and the image intensity values at the 125 voxel locations may be associated with 125 feature elements for the point in the center of the patch;
High level features can be derived from one or more patches: these types of features can include a variety of feature descriptors known in the art, such as a SIFT (Scale-invariant feature transform), a SURF (Speeded Up Robust Features), a GLOH (Gradient Location and Orientation Histogram), a LBP (local binary patterns), or a HOG (Histogram of Oriented Gradients), and the like. Such features may be computed for each 2D image slice that contains a voxel under consideration, and furthermore, such features may in an embodiment be extended to a 3D image;
Texture features: such as energy, entropy, contrast, homogeneity, and correlation of local image grayscale co-occurrence matrix, as well as those computed through filtering the image with Gabor filters, etc.;
Joint features: such as when a plurality of MR images (e.g., T1-weighted, T2-weighted, etc.) are associated with a given training subject. In such cases, features such as an intensity, a patch, a texture, etc., may be extracted from each MR scan independently for later combination. Additionally, features that characterized the correlation between the plurality of MR scans may be computed at each voxel location, e.g., a local joint histogram, and/or a local cross-correlation, or a co-variance of multiple MR channels;
Features derived from a convolution of images with at least one linear or non-linear filter (e.g., a local phase, gradients, a curvature, an edge-detector, or a corner-detectors, and the like);
Features derived by a transformation of the images (e.g., a Fourier transform, a Hilbert transform, a Radon transform, a distance transform, a discrete cosine transform, a wavelet transform, and the like);
Region co-variance features: a co-variance of any of the above point-wise features within a local sub-region; and
Classification-based features, discussed more fully below.

As shown in FIG. 2, the collection of features associated with an MR image voxel may be represented in a single vector (e.g., vector associated with voxel i, voxel i+1, . . . , voxel M).

Returning to FIG. 1, upon extraction of the image features, the MR feature vectors 120 may have multiple dimensions (e.g., each feature element in a feature vector may be considered as a dimension, as shown in FIG. 2). However, when the number of extracted features from the MR images increases, the task of creating a predictive model may become more difficult to accomplish. This is because each patient image normally contains millions of voxels, and each voxel may be associated with a large number of features. Therefore, if features extracted from all voxels of all the images from all the plurality of existing patients are used to build the predictive model, the computational cost for processing such huge amount of data can be very expensive. As a result, the practical number of dimensions depends on the processing power of the computer available relative to the computational cost. In addition, the performance of the predictive model resulting from processing the extracted features may not be proportional to the number of feature dimensions. In some cases, as the number of feature dimensions increases, the performance of predictive models may decrease because the effect of one feature may be cancelled or weakened by another feature if both are included in the processing. A large number of features may also cause unacceptable computational costs in using the prediction model to determine pseudo-CT images based on new MR data. Thus, in an embodiment, a dimensionality reduction module 132 may be used to generate reduced dimension feature vectors 140 without substantial loss of discriminative information provided by the MR features. The dimensionality reduction module 132 can be used to capture most of the relevant information from an original feature vector when reducing the original number of dimensions. For example, some dimensions of the MR feature vectors 120 may include noise or other information irrelevant to generating pseudo-CT images that can be removed. Other dimensions may include redundant information that can be combined or streamlined for a more compact representation of the distinctive information provided by the features. For example, if the original data fit a Gaussian distribution, the overall dimension of the original data may be reduced by representing the original data using the mean and standard deviation of the original data. Such a dimension reduction method causes the original data to be transformed. In some embodiments, the level of reduction in dimensionality can range from using the original feature vectors (i.e., no reduction) to any predetermined level of dimensionality (e.g., a reduced set of feature vectors). Thus, in an embodiment, the dimensionality reduction module 132 may be optional and the original feature vectors can be used to produce the pseudo-CT model 150.

If the dimensionality reduction module 132 is utilized, dimensionality reduction techniques used by model 132 may include at least two types of techniques: (1) unsupervised dimensionality reduction and (2) supervised dimensionality reduction. Typically, supervised dimensionality reduction is better than unsupervised dimensionality reduction, as described below.

Unsupervised dimensionality reduction may remove insignificant noise and data redundancy and require only MR feature vectors 120 as input. Common unsupervised dimensionality reduction techniques include, for example, principal component analysis (PCA), and its nonlinear version, kernel principal component analysis (KPCA).

Supervised dimensionality reduction may utilize other data of interest to further filter out dimensions irrelevant to generate a pseudo-CT image. For example, CT values 130 may be used for dimensionality reduction. CT values 130 (e.g., the original CT values or CT numbers) may be obtained from the CT scan data of training data 110. Supervised dimensionality reduction may take both MR feature vectors 120 and CT values 130 as input. Possible supervised dimensionality reduction techniques include, for example: canonical component analysis (CCA), metric learning (ML) methods, supervised principal component analysis (SPCA), locality sensitive hashing (LSH), local sensitive discriminative analysis (LSDA), etc. For dimensionality reduction techniques that require the data of interest to be associated with discrete class labels, image segmentation may be applied to the CT or MR scans in training data 110, resulting in segmentation classes that may be used as the class labels.

CT values 130 may be utilized by the dimensionality reduction module 132 to determine what signals in training data 110 are related to the underlying CT values. Using the original CT values, irrelevant signals can be suppressed while maintaining relevant signals. In general, at least one CT image for each training subject should be available. In some embodiments, multiple CT images may be available. A greater number of CT scans can be averaged to reduce image noise, thereby improving the effectiveness of dimensionality reduction module 132. The output of the dimensionality reduction module 132 is a reduced dimension feature vector 140.

Once the training data are collected and processed (e.g., subjected to image feature extraction, dimensionality reduction techniques, etc.), a pseudo-CT prediction model 150 can be built using either statistical learning or machine learning techniques. In one embodiment, regression analysis can be used to build the pseudo-CT prediction model 150. Regression analysis is a statistical process for estimating the relationships among variables. There are a number of known methods to perform regression analysis, for example: linear regression or ordinary least squares regression, among others, are "parametric" in that the regression function is defined in terms of a finite number of unknown model parameters that can be estimated from training data. For pseudo-CT image generation, a regression model (e.g., Equation 1) can be defined, for example, as:

$$H \approx f(X, \beta), \quad \text{(Equation 1)}$$

where "H" denotes the CT values, "X" denotes a vector of input variables (e.g., any one of MR feature vectors 120 or reduced dimension feature vectors 140), and "$\beta$" denotes a vector of unknown parameters to be determined or trained for the regression model. In an embodiment, the CT values may be Hounsfield values for a CT scan.

Training data 110 that include MR scans and CT scans provide a set of known H values (e.g., CT values associated with a training subject's CT scans) having corresponding X values (e.g., feature vectors extracted from the MR scans of the same training subject). Using these data, the model parameter $\beta$ can be computed using data fitting techniques such as least squares, maximum likelihood or the like. Once $\beta$ is estimated, the model can then compute H (e.g., pseudo-CT values) for a new set of X values (e.g., feature vectors extracted from a new MR scan).

In another embodiment, machine learning and supervised learning can be used for building the pseudo-CT prediction model 150. Supervised learning is a branch of machine learning that infers a prediction model given a set of training data. Each sample of the training data is a pair consisting of input data (e.g., a vector of measurements or features) and a desired output value (also called a supervisory signal). A supervised learning algorithm analyzes the training data and produces a predictor function, which is a regression function when the output variable is numeric or is continuous. Consistent with disclosed embodiments, many different algorithms can be applied, including but not limited to: kNN (k-nearest neighbors) regression, support vector machines, neural networks, decision trees, random forests, and gradient boosting machines.

Figure 3:
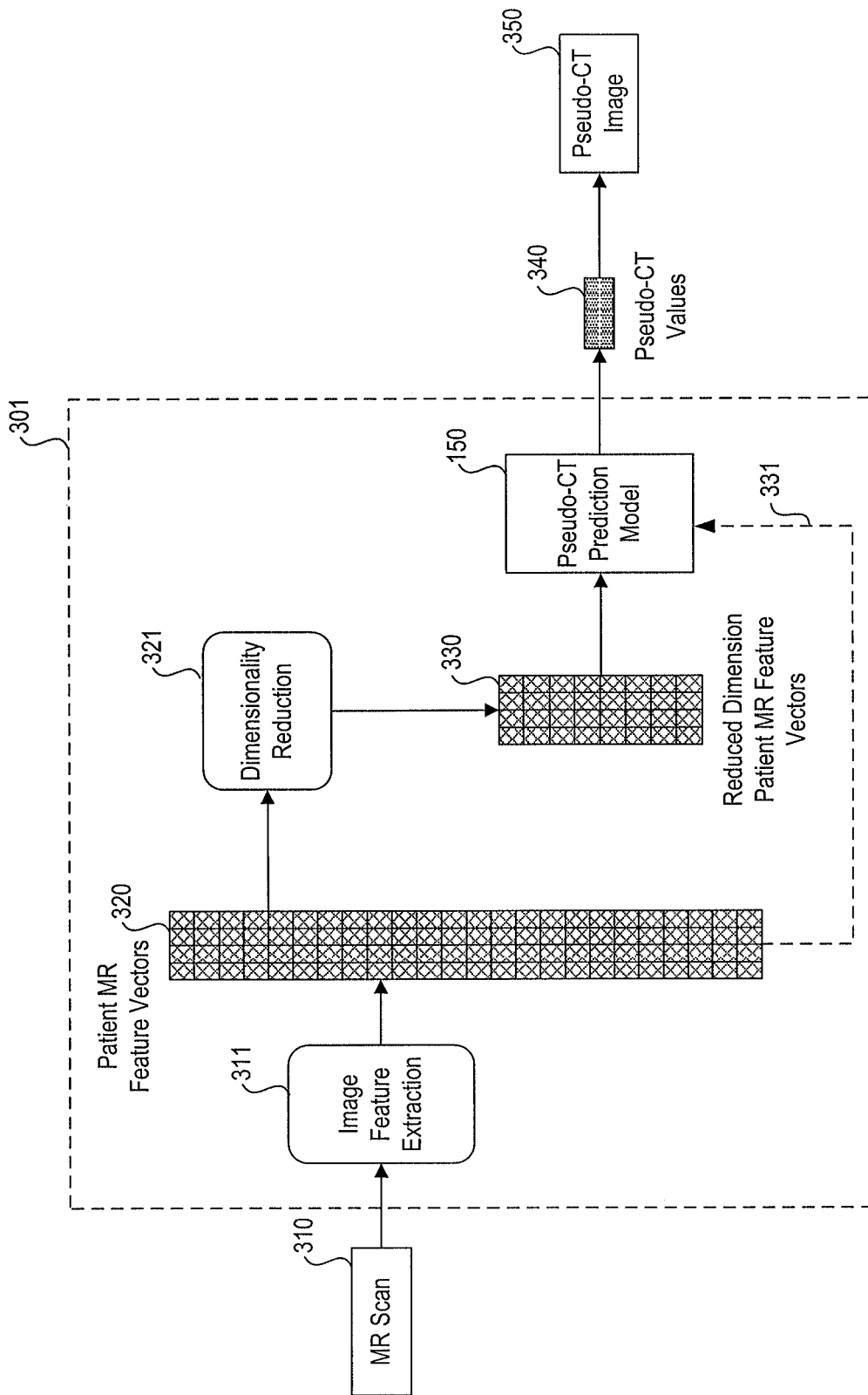
FIG. 3 is a diagram of an exemplary process for using the prediction module of FIG. 1 to generate a pseudo-CT image of a patient.

FIG. 3. Illustrates a flowchart of an exemplary process for a prediction module that can use the Pseudo-CT model 150, consistent with the disclosed embodiments. Once the pseudo-CT model 150 is created and trained, the model 150 can be used by the prediction module 301 in an application stage to generate a pseudo-CT image from a new MR scan, either for the same patient or for a new patient. As shown in FIG. 3, the process of generating the pseudo-CT image 350 is similar to the process described above for FIG. 1, except that the pseudo-CT prediction model 150 previously generated and trained is utilized in the application stage. In the process, a new MR scan 310 is input into the prediction module 301. In an embodiment, the prediction module 301 can include an image feature extraction module 311 and the pseudo-CT prediction model 150. In this embodiment, the MR scan 301 has no corresponding CT scan. Features can be extracted from MR scan 301 to generate patient MR feature vectors 320 in a similar manner to that discussed above with respect to generation of MR feature vectors 120. A dimensionality reduction module 321 can be included to reduce the dimensions of the patient MR feature vectors 320. Alternatively, the patient MR feature vectors 320 may be used by the pseudo-CT prediction model 150 without any reduction in dimensionality, as indicated by dash line 331.

In this way, the prediction module 301 uses the pseudo-CT prediction model 150 developed during the training stage to predict a pseudo-CT value at each location of the patient MR image 310, as no CT scan was originally provided corresponding to the new MR scan. Because the pseudo-CT prediction model 150 may operate "point-wise", e.g., at every image location, the pseudo-CT value represents a value derived based on a feature vector for a particular voxel at a particular location in the MR scan 310. The prediction model 301 can therefore generate pseudo-CT values 340. The pseudo-CT values 340 represent a plurality of intensity values for the pseudo-CT image 350. To generate the pseudo-CT image 350, the pseudo-CT values 340 are typically placed into their proper locations on a grid of voxels. In an embodiment, the prediction model 301 may predict some values (e.g., pseudo-CT values 340) of the voxel grid as the image is a grid of voxels (e.g., not every image voxel is predicted); and then interpolation may be used to generate the pseudo-CT image 350 to depict an accurate visual representation of the patient's anatomical details.

The pseudo-CT prediction model 150 can be trained once using training data 110 of all available patients and then the pseudo-CT prediction model 150 can be used for all future new patients. Alternatively, the same pseudo-CT prediction model 150 may not be used for every patient. A pseudo-CT prediction model 150 may be customized for a particular patient. For example, the training data may be selected to include data most similar or relevant to the new patient and a model can be built specific for the new patient.

Figure 4A:
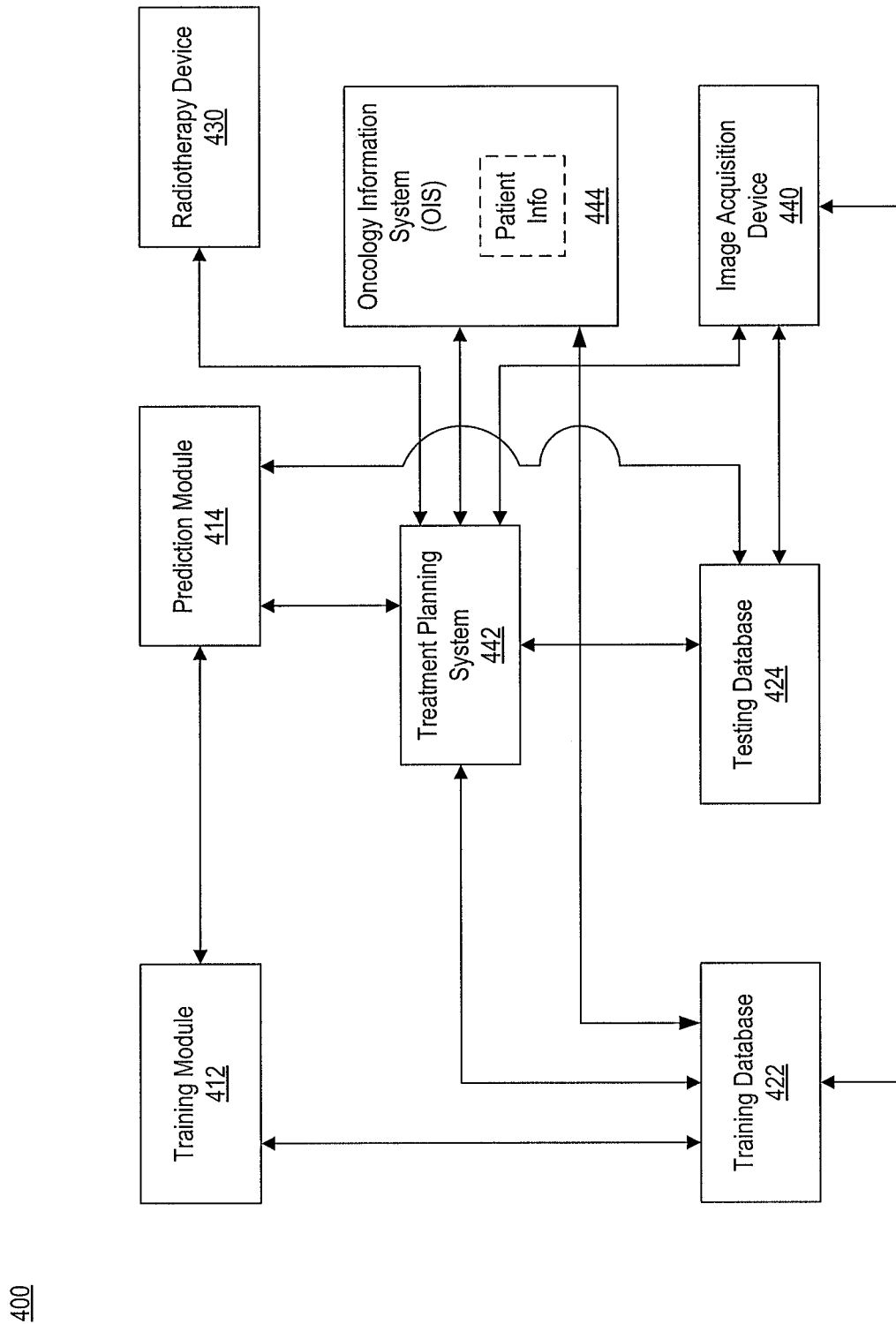
FIG. 4A illustrates an exemplary radiotherapy system.

FIG. 4A illustrates an exemplary radiotherapy system 400, according to some embodiments of the present disclosure. Radiotherapy system 400 may include a training module 412, a prediction module 414, a training database 422, a testing database 424, a radiotherapy device 430, and an image acquisition device 440. Radiotherapy system 400 may also be connected to a treatment planning system (TPS) 442 and an oncology information system (OIS) 444, which may provide patient information. In addition, radiotherapy system 400 may include a display device and a user interface (not shown).

Figure 4B:
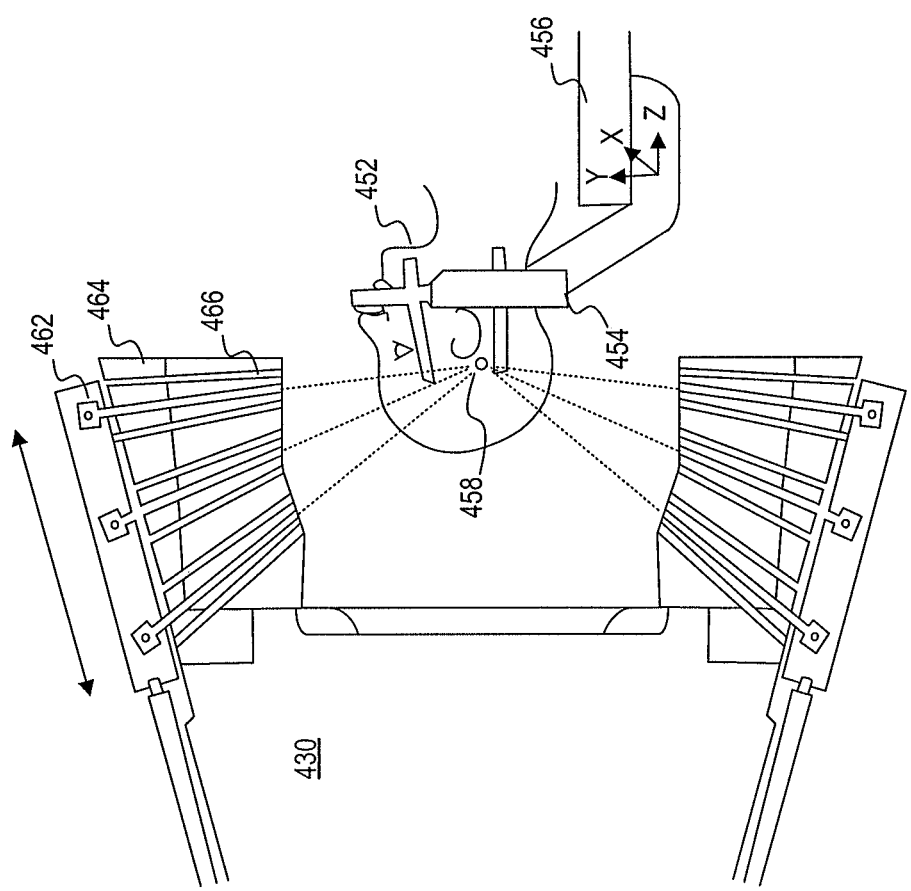
FIG. 4B illustrates an exemplary radiotherapy device, a Gamma Knife.

FIG. 4B illustrates an example of one type of radiotherapy device 430 (e.g., Leksell Gamma Knife manufactured by Elekta, AB, Stockholm, Sweden), according to some embodiments of the present disclosure. As shown in FIG. 4B, in a radiotherapy treatment session, a patient 452 may wear a coordinate frame 454 to keep stable the patient's body part (e.g., the head) undergoing surgery or radiotherapy. Coordinate frame 454 and a patient positioning system 456 may establish a spatial coordinate system, which may be used while imaging a patient or during radiation surgery. Radiotherapy device 430 may include a protective housing 464 to enclose a plurality of radiation sources 462. Radiation sources 462 may generate a plurality of radiation beams (e.g., beamlets) through beam channels 466. The plurality of radiation beams may be configured to focus on an isocenter 458 from different directions. While each individual radiation beam may have a relatively low intensity, isocenter 458 may receive a relatively high level of radiation when multiple doses from different radiation beams accumulate at isocenter 458. In certain embodiments, isocenter 458 may correspond to a target under surgery or treatment, such as a tumor. The radiotherapy device 430 (e.g., Leksell Gamma Knife manufactured by Elekta, AB, Stockholm, Sweden), may, in an embodiment, utilize MR images with assigned bulk densities, or CT images fused with MR images, and may use pseudo-CT images generated consistent with the disclosed embodiments.

Figure 4C:
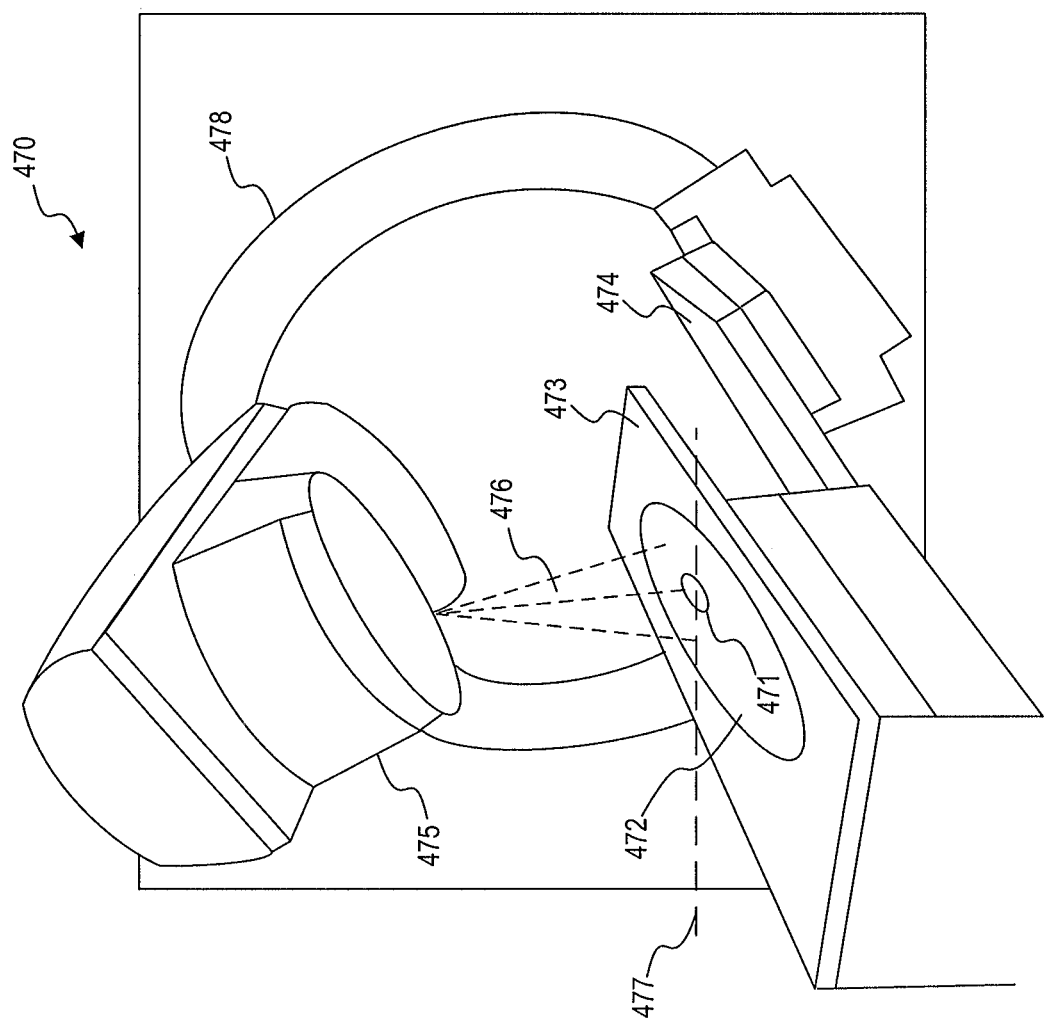
FIG. 4C illustrates an exemplary radiotherapy device that is a linear accelerator.

FIG. 4C illustrates another example of a radiotherapy device 430 (e.g., a linear accelerator 470), according to some embodiments of the present disclosure. Using a linear accelerator 470, a patient 472 may be positioned on a patient table 473 to receive the radiation dose determined by the treatment plan. Linear accelerator 470 may include a radiation head 475 that generates a radiation beam 476. The entire radiation head 475 may be rotatable around a horizontal axis 477. In addition, below the patient table 473 there may be provided a flat panel scintillator detector 474, which may rotate synchronously with radiation head 475 around an isocenter 471. The intersection of the axis 477 with the center of the beam 476, produced by the radiation head 475, is usually referred to as the isocenter. The patient table 473 may be motorized so that the patient 472 can be positioned with the tumor site at or close to the isocenter 471. The radiation head 475 may rotate about a gantry 478, to provide patient 472 with a plurality of varying dosages of radiation according to the treatment plan. In an alternative embodiment, the linear accelerator 470 may be a MR-linear accelerator ("MR-LINAC"). Both the linear accelerator 10 and the MR-LINAC may in an embodiment, utilize MR images, CT images, and may use pseudo-CT images generated consistent with the disclosed embodiments.

Figure 5:
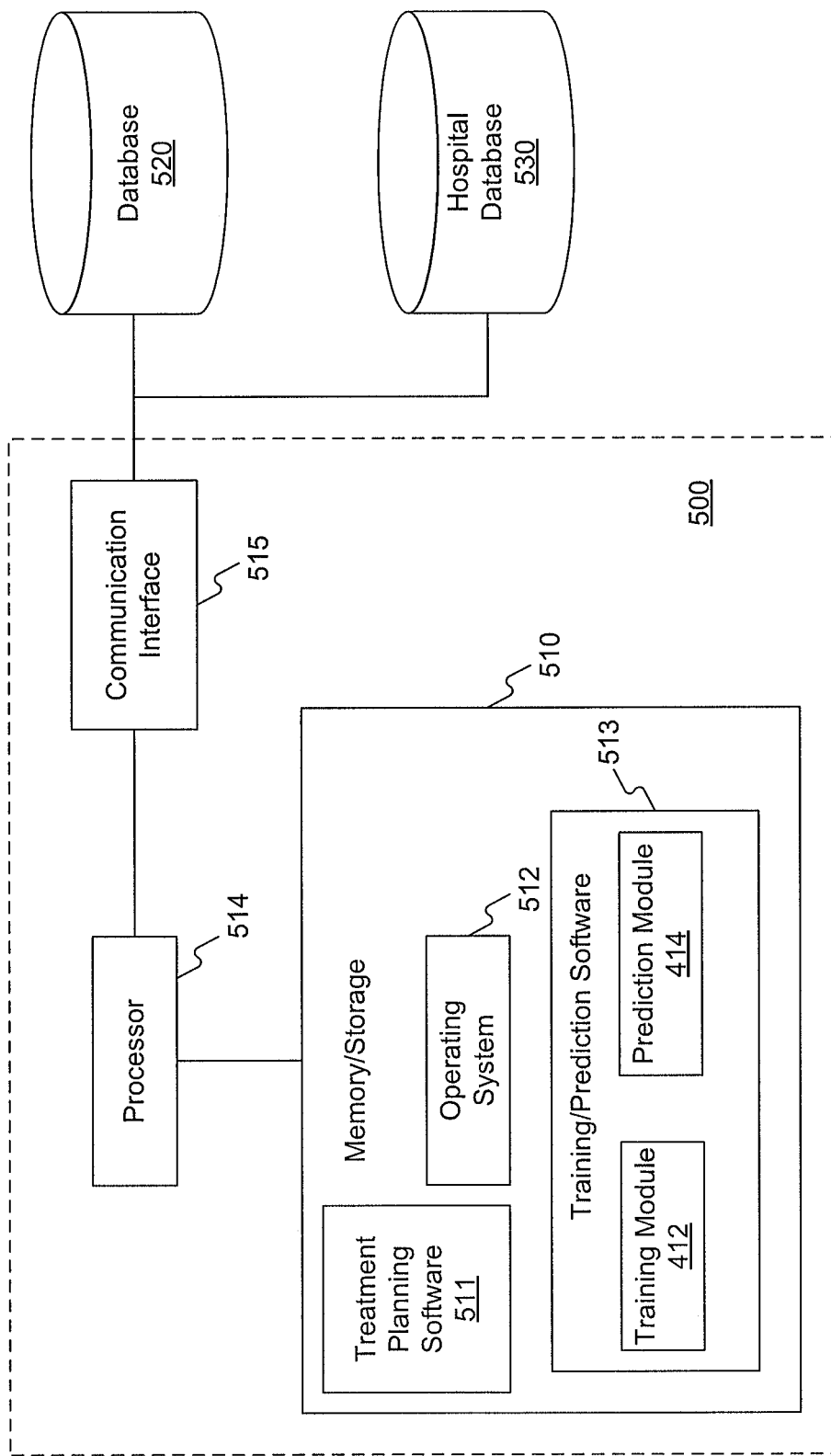
FIG. 5 illustrates an exemplary system for building a pseudo-CT predictive model and generating pseudo-CT images.

FIG. 5 is an exemplary system 500 for building a pseudo-CT predictive model and generating pseudo-CT images, consistent with the disclosed embodiments. According to some embodiments, system 500 may be one or more high-performance computing devices capable of identifying, analyzing, maintaining, generating, and/or providing large amounts of data consistent with the disclosed embodiments. System 500 may be standalone, or it may be part of a subsystem, which in turn may be part of a larger system. For example, system 500 may represent distributed high-performance servers that are remotely located and communicate over a network, such as the Internet, or a dedicated network, such as a LAN or a WAN. In some embodiments, system 500 may include an embedded system, MR scanner, and/or touchscreen display device in communication with one or more remotely located high-performance computing devices.

In one embodiment, system 500 may include one or more processors 514, one or more memories 510, and one or more communication interfaces 515. Processor 514 may be a processing device, include one or more general-purpose processing devices such as a microprocessor, central processing unit (CPU), graphics processing unit (GPU), or the like. More particularly, processor 514 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 514 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 514 may be a special-purpose processor, rather than a general-purpose processor. Processor 514 may include one or more known processing devices, such as a microprocessor from the Pentium™ or Xeon™ family manufactured by Intel™, the Turion™ family manufactured by AMD™, or any of various processors manufactured by Sun Microsystems. Processor 514 may also include graphical processing units manufactured by Nvidia™. The disclosed embodiments are not limited to any type of processor(s) otherwise configured to meet the computing demands of identifying, analyzing, maintaining, generating, and/or providing large amounts of imaging data or any other type of data consistent with the disclosed embodiments.

Memory 510 may include one or more storage devices configured to store computer-executable instructions used by processor 514 to perform functions related to the disclosed embodiments. For example, memory 510 may store computer executable software instructions for treatment planning software 511, operating system software 512, and training/prediction software 513. Processor 514 may be communicatively coupled to the memory/storage device 510, and the processor 514 may be configured to execute the computer executable instructions stored thereon to perform one or more operations consistent with the disclosed embodiments. For example, processor 514 may execute training/prediction software 513 to implement functionalities of training module 412 and prediction module 414. In addition, processor device 514 may execute treatment planning software 511 (e.g., such as Monaco® software manufactured by Elekta) that may interface with training/prediction software 513.

The disclosed embodiments are not limited to separate programs or computers configured to perform dedicated tasks. For example, memory 510 may include a single program that performs the functions of the system 500 or multiple programs (e.g., treatment planning software 511 and/or training/prediction software 513). Additionally, processor 514 may execute one or more programs located remotely from system 500, such as programs stored in database 520, such remote programs may include oncology information system software or treatment planning software. Memory 510 may also store image data or any other type of data/information in any format that the system may use to perform operations consistent with the disclosed embodiments.

Communication interface 515 may be one or more devices configured to allow data to be received and/or transmitted by system 500. Communication interface 515 may include one or more digital and/or analog communication devices that allow system 500 to communicate with other machines and devices, such as remotely located components of system 500, database 520, or hospital database 530. For example, Processor 514 may be communicatively connected to database(s) 520 or hospital database(s) 530 through communication interface 515. For example, Communication interface 515 may be a computer network, such as the Internet, or a dedicated network, such as a LAN or a WAN. Alternatively, the communication interface 515 may be a satellite communications link or any form of digital or analog communications link that allows processor 514 to send/receive data to/from either database(s) 520, 530.

Database(s) 520 and hospital database(s) 530 may include one or more memory devices that store information and are accessed and managed through system 500. By way of example, database(s) 520, hospital database(s) 530, or both may include relational databases such as Oracle™ databases, Sybase™ databases, or others and may include non-relational databases, such as Hadoop sequence files, HBase, Cassandra or others. The databases or other files may include, for example, raw data from MR scans or CT scans associated with training subjects, MR feature vectors 120, CT values 130, reduced-dimension feature vectors 140, pseudo-CT prediction model(s) 150, pseudo-CT value(s) 340, pseudo-CT image(s) 350, DICOM data, etc. Systems and methods of disclosed embodiments, however, are not limited to separate databases. In one aspect, system 500 may include database(s) 520 or hospital database(s) 530. Alternatively, database(s) 520 and/or hospital database(s) 530 may be located remotely from the system 500. Database(s) 520 and hospital database(s) 530 may include computing components (e.g., database management system, database server, etc.) configured to receive and process requests for data stored in memory devices of database(s) 520 or hospital database(s) 530 and to provide data from database(s) 520 or hospital database(s) 530.

System 500 may communicate with other devices and components of system 500 over a network (not shown). The network may be any type of network (including infrastructure) that provides communications, exchanges information, or facilitates the exchange of information and enables the sending and receiving of information between other devices and/or components of system 500 over a network (not shown). In other embodiments, one or more components of system 500 may communicate directly through a dedicated communication link(s), such as a link (e.g., hardwired link, wireless link, or satellite link, or other communication link) between system 500 and database(s) 520 and hospital database(s) 530.

The configuration and boundaries of the functional building blocks of system 500 has been defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Figure 6:
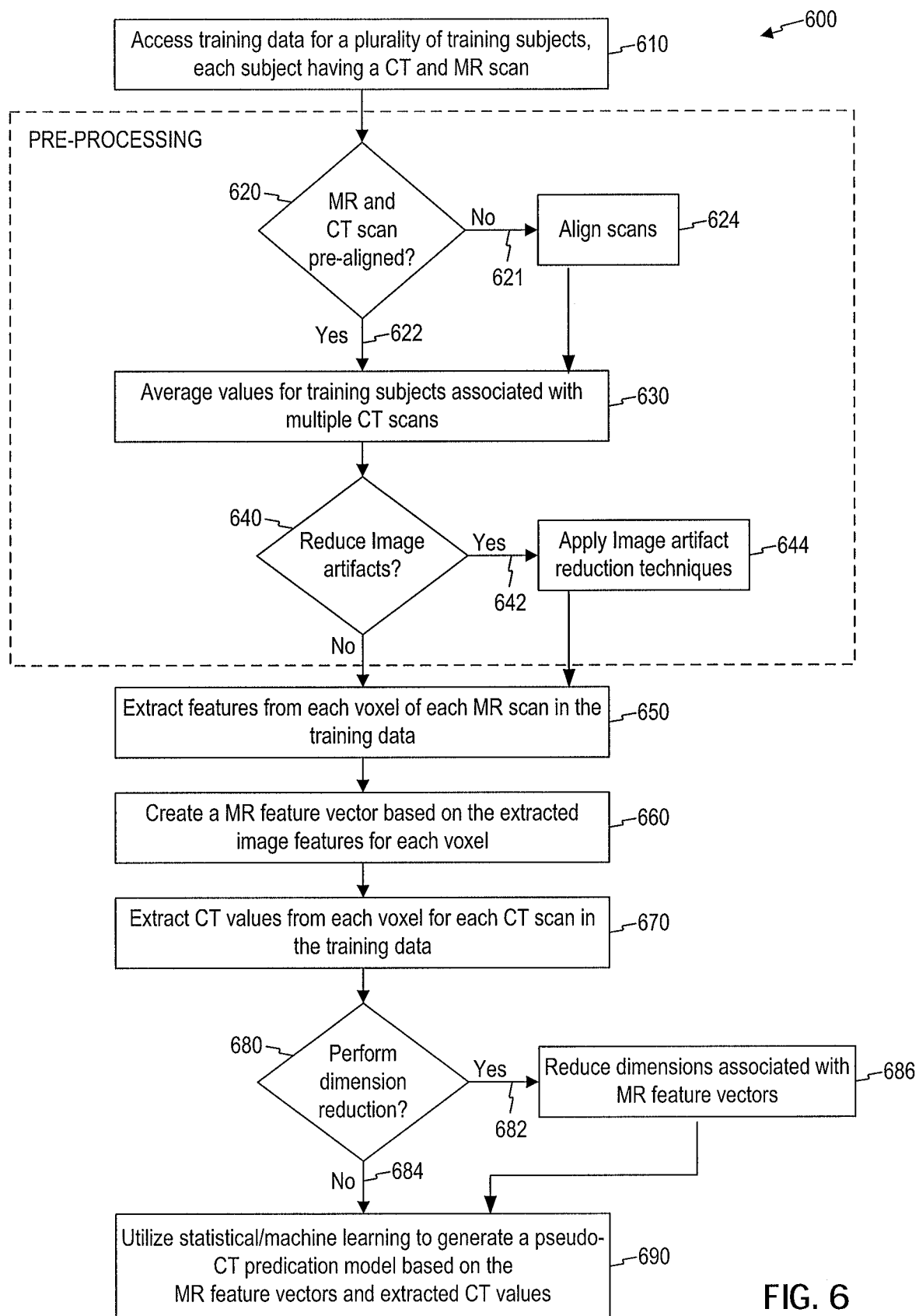
FIG. 6 is a flowchart of an exemplary process for training and building a pseudo-CT predictive model.

FIG. 6 is a flowchart of an exemplary process 600 for training and building a pseudo-CT predictive model, consistent with the disclosed embodiments. Process 600 includes a plurality of steps, some of which may be optional. At step 610, system 500 may access training data 110 associated with a plurality of training subjects from, for example, database 520 and/or hospital database 530. The training data 110 may include at least one MR scan and at least one CT scan for each training subject (e.g., as shown in FIG. 1, training subject data $110a$-$110_N$). In some embodiments, the training data 110 may include at least one MR scan and multiple CT scans for the same patient.

According to some embodiments, system 500 may determine whether some or all of the training data 110 require preprocessing before being used to train and build the pseudo-CT prediction model 150. At step 620, processor 514 determines whether the MR scans and the corresponding CT scans for one or more of the training subjects in the training data are aligned (e.g., for each MR voxel, the CT value(s) from the corresponding CT voxel are known). If the MR and CT images are not aligned, process 600 follows branch 621 (e.g., "NO") to align the scans at step 624. System 600 may align the MR scan and corresponding CT scan(s) according to methods known to those of skill in the art, as needed. Alternatively, if the MR and CT image(s) are aligned, process 600 follows branch 622 (e.g., "YES") continues to step 630.

Optionally, at step 630, processor 514 verifies if the training data 110 include multiple CT scans for the same training subject. If there are multiple CT scans, then processor 514 determines the average CT values for corresponding CT voxels between the multiple CT scans in order to reduce image noise for the same patient. Otherwise, process 600 proceeds directly from step 620 to step 640.

At step 640, as part of pre-processing, processor 514 determines whether to reduce or eliminate image artifacts from the MR scans based on, for example, system settings reflected in treatment planning software 511 or training/prediction software 513. If reduction of image artifacts is desired, process 600 follows branch 642 ("YES") to step 644. At step 644, processor 514 may apply, as part of pre-processing, image artifact reduction techniques. By pre-processing the MR scans, processor 514 can remove or reduce image artifacts, such as intensity non-uniformity (also known as MR image bias field) and image noise. In addition, pre-processing can normalize/standardize MR image intensity values across different MR scanner types (e.g., manufactured by GE, Siemens and the like; or various magnetic field strengths such as 0.5 Tesla, 1.5 Tesla, etc.). Pre-processing techniques can also be used for removing or reducing image artifacts for new patent MR scan 310 (shown in FIG. 3). If image artifact reduction is not conducted, process 600 continues to step 650 to extract features. In some embodiments, one or more steps of the pre-processing (e.g., as enclosed by the dash lines in FIG. 6) may be omitted.

At step 650, features can be extracted from the training data 110. In some embodiments, system 500 may extract features from every voxel of each MR scan in the training data 110. For example, the MR image itself can be used and each voxel or selected voxels from the MR image can be used to extract features. Alternatively, processor 514 may segment the MR image into different tissue types and segment the image voxels of each MR scan based on tissue types. This can be advantageous in some cases because the tissue types can be used as an additional feature, for example, in addition to other extracted features.

At step 660, system 500 may create an MR feature vector based on the extracted image features for each voxel of the MR scan. Therefore, a vector containing a plurality of features for each voxel of the MR scan can be produced by processor 514. A plurality of MR feature vectors 120 can be produced by processor 514 for a plurality of voxels of the MR scan.

At step 670, system 500 may extract a CT value from each voxel of each CT scan in the training data.

At step 680, system 500 may determine whether to reduce the number of dimensions associated with the MR feature vectors 120.

For example, processor 514 of system 500 may determine that the number of dimensions associated with MR feature vectors 120 would lead to a high computational cost or potentially cause performance problems when processed by the pseudo-CT predictive model 150. In another example, system 500 may determine that MR feature vectors 120 include noise or duplicated data exceeding thresholds considered to affect the accuracy of pseudo-CT predictive model 150. In another embodiment, system 500 may determine whether to conduct dimensionality reduction based on factors affecting performance and/or output quality. Therefore, if processor 514 determines that dimensionality reduction is required, process 600 follows branch 682 (e.g., "YES") to step 686, in which processor 514 can reduce the dimensions associated with MR feature vectors 120. Alternatively, in some embodiments, system 500 may receive input (e.g., from a user) to not perform any dimensionality reduction of the MR feature vectors 120.

If no dimensionality reduction is required, process 600 may proceed directly along branch 684 to step 690. At step 690, system 500 may utilize statistical or machine learning techniques to generate a pseudo-CT prediction model 150 based on the MR feature vectors (e.g., 120) and extracted CT values. In some embodiments, the reduced-dimension feature vectors 140 may be utilized.

According to some embodiments, a subset of training data 110 may be used as a basis to train and build the pseudo-CT prediction model 150. Thus, system 500 may determine (e.g., based on user input and/or system settings reflected in treatment planning software 511 and/or training/prediction software 513) a subset of training data 110 to train and build the pseudo-CT prediction model 150. In another embodiment, the subset of training data 110 can be classified based on particular image regions. For example, the subset of training data 110 can be: 1) with respect to particular anatomical regions, 2) with respect to various tissue classifications, or 3) with respect to training subject characteristics.

For example, one or more features may provide superior interpretation of the underlying anatomical structure for a given patient MR scan; and thus, only the subset of superior features may be extracted from training data 110 for use in training pseudo-CT prediction model 150. Using the superior features, the predictive power of pseudo-CT prediction model 150 to estimate corresponding pseudo-CT values 340 for the given patient MR scan may be improved. The subset of features can be used to generate and train one or more pseudo-CT models.

In an embodiment, when building a pseudo-CT prediction model with respect to a particular anatomical region, a subset of training data 110 (e.g., only training data 110 associated with the body region of interest) may be used to train and build the pseudo-CT prediction model 150. Instead of one pseudo-CT prediction model, processor 514 can generate a plurality of pseudo-CT prediction models with respect to particular anatomical areas of the body (e.g., head, upper body, lower body, and the like). Thus, processor 514 can utilize the MR feature vectors 120 (or reduced dimension feature vectors 140) and the CT values 130 for a predetermined anatomical location of interest to generate a pseudo-CT prediction model 150 for that particular anatomical location of interest depicted in the MR scan.

For example, system 500 may determine that the patient MR scan 310 includes an MR image of the patient's prostate. Thus, consistent with disclosed embodiments, system 500 may identify a pseudo-CT prediction model that has been built and trained based on training data 110 utilizing one or more MR scans and CT scans of a prostate as training data. In an embodiment, more than one pseudo-CT prediction model may be available, where each model may depict various anatomical aspects of a prostate, for example. Therefore, a plurality of pseudo-CT prediction models may be generated, where each pseudo-CT prediction model is for a particular anatomical area (e.g., a pseudo-CT prediction model for a prostate, a pseudo-CT prediction model for a right lung, a pseudo-CT prediction model for a left lung, a pseudo-CT prediction model for a brain, and the like).

In another embodiment, the pseudo-CT predictive model 150 may be generated based on classification-based features, such as a tissue classification. For instance, system 500 may use the image feature extraction module 111 to segment the image voxels of each MR scan in the training data 110, according to a tissue class (e.g., bone, fat, muscle, water, air, and structural classes such as cardiac tissue, lung tissue, liver tissue, brain tissue, and the like). A plurality of segmentation maps for each MR scan can be generated based on the segmented image voxels. The image features can be extracted from the segmentation maps. The segmentation map extracted image features may be combined with the MR scan extracted image features for each voxel. The MR feature vectors may be determined for each training subject based on the combined image features. A pseudo-CT prediction model based on the combined MR feature vectors and extracted CT values can be generated. As stated above, the term "tissue" is being used as a classification and not merely to suggest specific types of tissue (e.g., air is not a tissue).

In a still further embodiment, a process for generating pseudo-CT image(s) can be based on using training data selected according to training subject characteristics. For example, system 500 may identify one or more common characteristics among a subset of the training subjects. For example, system 500 may identify the age, gender, weight class, etc., associated with each training subject and select training subjects having one or more common characteristics. In other examples, system 500 may identify one or more characteristics of the training subjects based on the MR and CT scan(s) in the training data 110. Further, system 500 may identify one or more characteristics of the patient (e.g., a new patient) in common with a subset of the training subjects. For example, system 500 may identify one or more characteristics of the patient and compare the patient's characteristics with those identified for the training subjects to identify common characteristics. System 500 may then select training subjects having the one or more common characteristics as training data to train and build pseudo-CT prediction model 150.

Image features may be extracted from the MR scans and CT numbers from the CT scans associated with the characteristics of training subjects. For example, system 500 may extract image features from MR scans and CT values 130 from CT scans in training data 110 associated with a subset of the training subjects having common characteristics with the new patient. Then, MR feature vectors can be determined for each training subject of the subset based on the extracted image features. Pseudo-CT prediction model can be generated based on these MR feature vectors and extracted CT values.

The pseudo-CT prediction model 150 can be trained using all training data 110 and then utilized for a new MR scan for a new patient. The pseudo-CT prediction model 150 can also be used for all future new patients. In some embodiments, the same pseudo-CT prediction model 150 may not be used for every patient. A pseudo-CT prediction model 150 may be custom generated for a particular patient. For example, the training data may be selected based on training subjects that are similar or relevant to the new patient and a model can be built specifically for the new patient.

Medical personnel can find it useful to assess both the MR characteristics and the CT characteristics of a region of interest in a patient to determine an optimal treatment or diagnosis. Further, the pseudo-CT model can be used to derive a CT image from an MR image to facilitate patient dose computation in radiation therapy treatment planning. This is desirable for accurately generating a pseudo-CT image from an MR image in order for patients to be spared from additional radiation exposure arising from CT imaging. In order to replace a real CT image, the pseudo-CT image should be as close as possible to a real CT image of the patient for the purpose of dose computation in radiation therapy treatment planning or for generating digitally reconstructed radiographs (DRRs) for image guidance. However, there is not a simple mathematical relationship between CT image intensity values (CT values) and MR intensity values. The difficulty arises because MR intensity values are not standardized and can vary significantly depending upon different MR scanner settings or different MR imaging sequence parameters.

Figure 7:
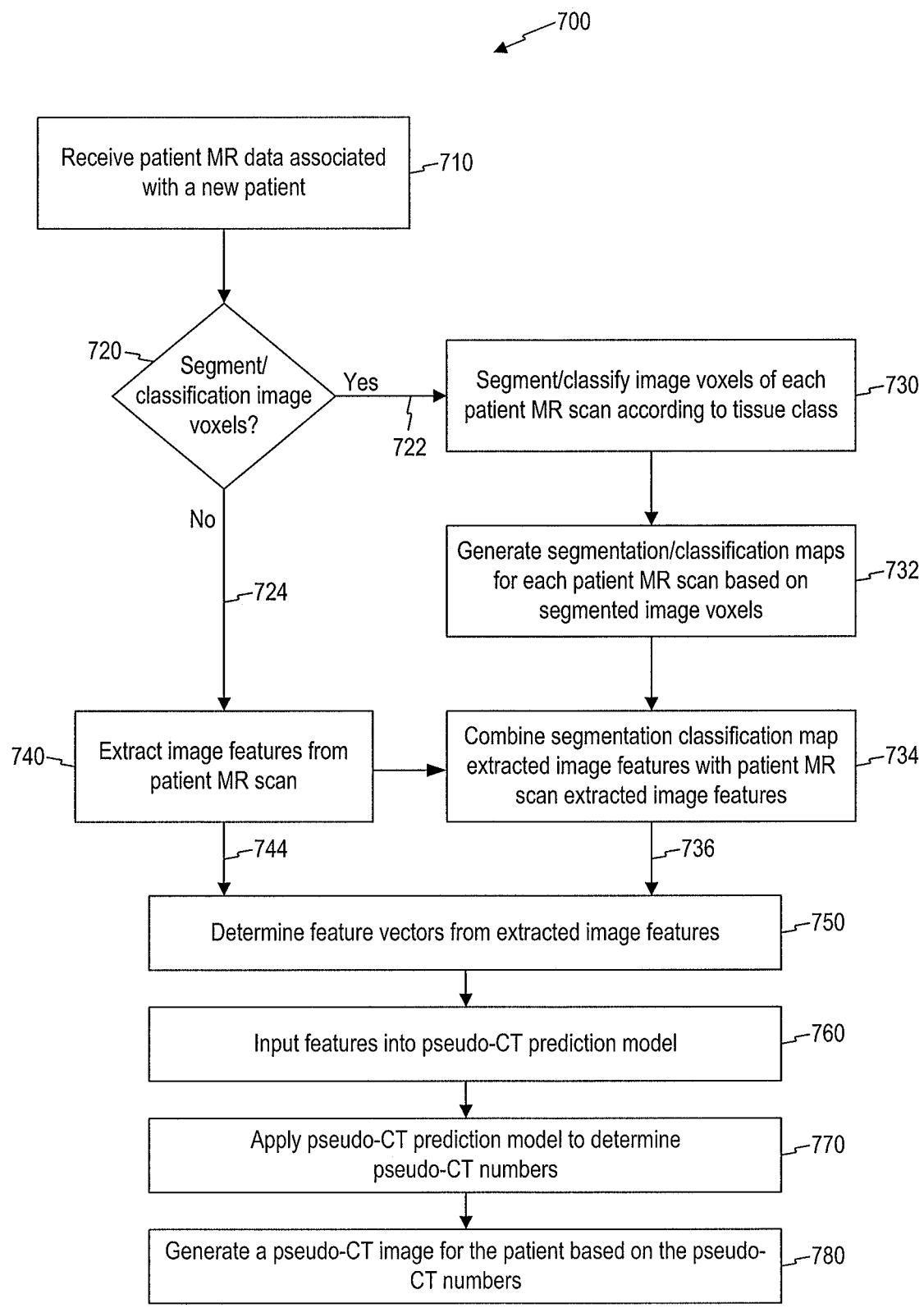
FIG. 7 is a flowchart of an exemplary process for using a pseudo-CT predictive model to generate a pseudo-CT image.

FIG. 7 is a flowchart of an exemplary process 700 for using the pseudo-CT predictive model (as described by FIG. 1 and FIG. 6) after the model has been trained to generate pseudo-CT values and pseudo-CT images (as described in FIG. 3), consistent with the disclosed embodiments. At step 710, system 500 may receive at least one MR scan (e.g., MR scan 310) associated with a patient (e.g., a new patient). The at least one MR scan may not have a corresponding CT scan. The MR scan is used to generate a pseudo-CT image.

At step 720, processor 514 may determine whether the MR image voxels should be segmented. Segmenting the MR scan is optional. Processor 514 can receive instructions from either the treatment planning software 511 (shown in FIG. 5) or from a user interface (not shown) to indicate whether the MR scan should be segmented. If so, process 700 follows branch 722 (e.g., "YES") to segment the MR scan. At step 730, the image voxels of the MR scan are segmented according to, for example, tissue classification. Segmentation can be performed according to segmentation techniques known to those of skill in the art. For example, processor 514 may employ a k-means clustering segmentation method, a fuzzy C-means segmentation method, and the like to create one or more segmentation maps.

Processor 514 may further use more advanced segmentation methods. For example, processor 514 may employ a learning-based or feature-based approach to perform segmentation, which may include building a classification prediction model using, for example, algorithms (e.g., local pattern feature, landmark feature, context feature, and the like) to predict a tissue label for each image voxel based on features of the image voxel.

At step 732, processor 514 may generate a plurality of segmentation maps for each MR scan based on the segmented image voxels to create a classification prediction model. For example, a binary bone segmentation map may be an image with values equal to "1" at voxels labeled as bones and "0" at all other voxels. The processor 514 may use the segmentation maps to extract additional features from the original MR images. Consistent with disclosed embodiments, learning-based methods disclosed above may be employed to train and build a predictive model for generating the one or more segmentation maps. Alternatively, if segmentation of the MR scan is not needed, process 700 follows branch 724 (e.g., "NO").

At step 740, processor 514 may extract image features from the patient's MR scan. If the optional path of segmenting the MR scan, described above, was performed, then the extracted image features can be provided along path 722. At step 734, processor 514 may combine the additional features extracted by using the segmentation map from the MR scan along with the features extracted directly from the MR images to form a combined set of features for each data point (e.g., voxel).

Regardless of whether the MR scan is segmented or not, after the image features have been extracted, process 700 proceeds (e.g., along path 744 or 736) to step 750. At step 750, processor 514 may determine feature vectors 120 for each training subject from the extracted image features.

At step 760, processor 514 may input the MR feature vectors 120 into pseudo-CT prediction model 150. At step 770, processor 514 may apply the pseudo-CT prediction model 150 to the input MR feature vectors 120 to determine the CT numbers (e.g., pseudo-CT values 340) for each voxel of the patient MR image 310.

At step 780, based on the pseudo-CT values 340, processor 514 may generate a pseudo-CT image 350 for the patient. The resulting pseudo-CT image 350 may be used for the purposes of dose computation in treatment planning, generating DRRs for image guidance, and the like.

Figure 8:
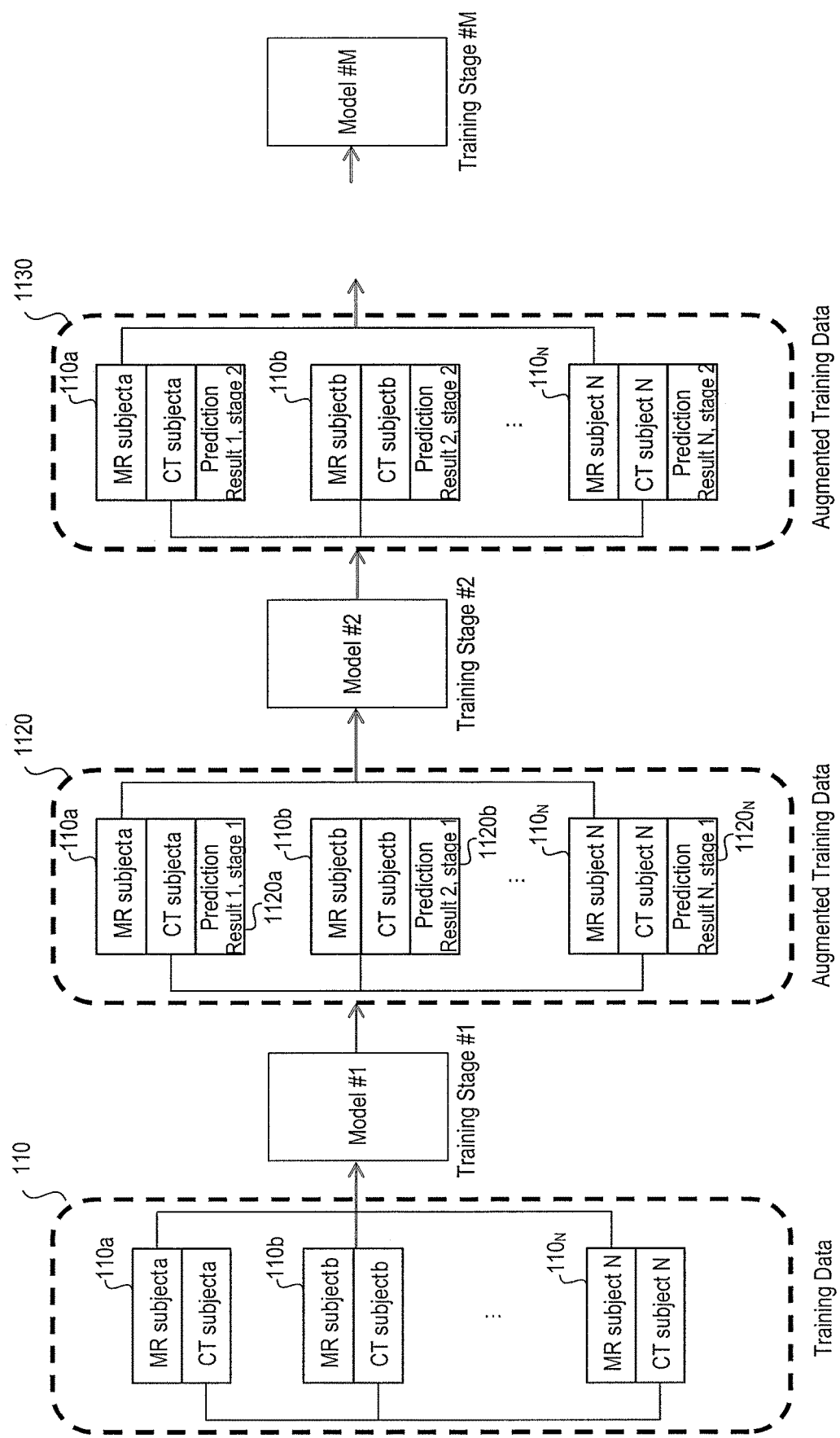
FIG. 8 is a diagram of an exemplary process for training and building a multi-stage pseudo-CT predictive model.

FIG. 8 illustrates a diagram of an exemplary method for augmenting training data to build a pseudo-CT predictive model, consistent with the disclosed embodiments. The method shown in FIG. 8 may also be referred to as a cascade training technique or a multi-stage training technique, in which an initially trained predictive model is used to produce an intermediate prediction result, which in turn is used as part of the training data to further refine the predicative model. The cascade training technique may include multiple training stages. In each stage a predictive model is trained using initial data (e.g., training data 110) combined with predication result produced by the predictive model generated in a prior stage.

In one embodiment, a pseudo-CT predictive model 150 may be initially built and trained using an initial set of training data, as described above with respect to FIG. 1. As part of the initial training process, image features are extracted from the plurality of image scans and feature vectors are determined from the extracted image features. In addition, the corresponding CT values can be determined from the CT scans. For example, at least one CT image for each training subject should be available. In an embodiment, multiple CT image may be available. If multiple CT image are available, the CT images can be averaged to reduce image noise. A pseudo-CT model may be trained in any stage of a cascade training process.

In another embodiment, a classification prediction model may be trained as an initial model or any intermediate model. As discussed above, the classification prediction model may be used to predict one or more segmentation maps, from which classification-based features may be extracted and used in the next training stage.

In an exemplary cascade training process, pseudo-CT predictive models and classification prediction models may be used in any combination among the multiple stages, so long as a pseudo-CT predictive model is trained and built in the last stage.

As shown in FIG. 8, the initially built predictive model is shown as Model #1. Model #1 is generated by processing the original training data, such as each MR scan, each CT scan, or each pair of MR and CT scans (e.g., 110*a*, 110*b*) during Training Stage #1. As discussed above, Model #1 may be a pseudo-CT predictive model or a classification prediction model. Model #1 can then be used in the training process of the next stage. For example, Model #1 can be used to generate a plurality of prediction results (e.g., prediction result 1, stage 1; prediction result 2, stage 1, . . . prediction result N, stage 1). For example, when Model #1 is a pseudo-CT predictive model, the MR scan of training subject a can be used as input (e.g., as if training subject a is a new patient and the MR scan of training subject a is a new MR scan) to Model #1 to generate a pseudo-CT prediction result 1120*a*: prediction result 1, stage 1. In another example, when Model #1 is a classification prediction model, the prediction result of Model #1 may a segmentation map. Other prediction results 1120*b* . . . 1120N can be similarly generated. These prediction results can then be augmented to the initial training data to form augmented training data 1120. For example, by associating the pairs of MR and CT scans (e.g., 110*a*, 110*b*, . . . 110N) with their corresponding prediction results (e.g., 1120*a*, 1120*b*, . . . 1120N) generated from Model #1, augmented training data 1120 can be created. The augmented training data 1120 can be used by a training module (e.g., training module 412) in the next training stage to generate another model (e.g., Model #2).

In this way, a new, refined, trained model can be generated (e.g., Model #2, Model #3, . . . Model #M) at each stage. The model developed at a previous stage can be refined by applying the augmented training data (e.g., augmented training data 1120, 1130, etc.) to the training module. For example, Model #2 can be generated using the augmented training data 1120 including the prediction results generated by Model #1. In order to generate Model #2, the augmented training data 1120 can be input into the training module (e.g., training module 412) in training stage #2. In some embodiments, the prediction result generated by Model #1 may be an image (e.g., a pseudo-CT image) or a map (e.g., a segmentation map) for each training subject. Image features may then be extracted from the prediction result (e.g., image or map) using, for example, image feature extraction module 111. The image features that can be extracted from the prediction result may include any features discussed in prior passages, such as intensity features, context features, patch features, local patter features, landmark features, etc. The features extracted from the prediction result may be combined with the features extracted from the original MR images to form a new, extended feature vector for each image point. The extended feature vector may be used in the next training stage to train, for example, Model #2. As each subsequent prediction model (e.g., Model #2) is built and trained using prediction results of its prior prediction model (e.g., Model #1), new information revealed from the prediction results can be added into the training process and the performance of the subsequent prediction model can be improved. This process of using augmented training data (e.g., augmented training data 1120, 1130, etc.) to train each successive model (e.g., Model #1, Model #2, . . . etc.) continues until a final prediction model Model #M is trained and built. If the goal of the cascade training process is to build a pseudo-CT prediction model, then the last model, Model #M is a pseudo-CT prediction model, while all other models in the intermediate stages can be any models. The number of stages utilized can depend upon the validation of the Model #M to accurately predict the CT values. For example, this iteration process can stop when the difference between pseudo-CT prediction values generated by the latest model and the original CT values is less than a predetermined threshold. In another example, the iteration process can stop when the difference between prediction results of successive pseudo-CT prediction models is less than a predetermined threshold.

As described above, the cascade training technique is applicable to training and building pseudo-CT prediction models and/or tissue classification models. When training and building tissue classification models, each intermediate predictive model (e.g., Model #1, Model #2, . . . Model #M−1) can be a tissue classification model that can, for example, provide segmentation maps reflecting tissue labels instead of producing pseudo-CT values. Using the multi-stage training process discussed above, each tissue classification model can be built and trained using the augmented data including the prior model's prediction results to continually refine the model at each stage. In addition, tissue classification and pseudo-CT prediction can be mixed into the multi-stage process. For example, in the first K stages, the model trained may be a tissue classification model and the prediction results may be tissue classification results. Once the tissue classification model is trained, the tissue classification result may then be used in the K+1 stage to predict the pseudo-CT values, where the tissue classification result can be used to extract a set of features together with other features extracted from the MR scans. A single extra stage may be performed (e.g., if M=K+1) or additional stages may be performed until M stages are reached (e.g., if M>K+1). At the end of the process, the final prediction model, Model #M is trained and built to generate pseudo-CT values.

Figure 9:
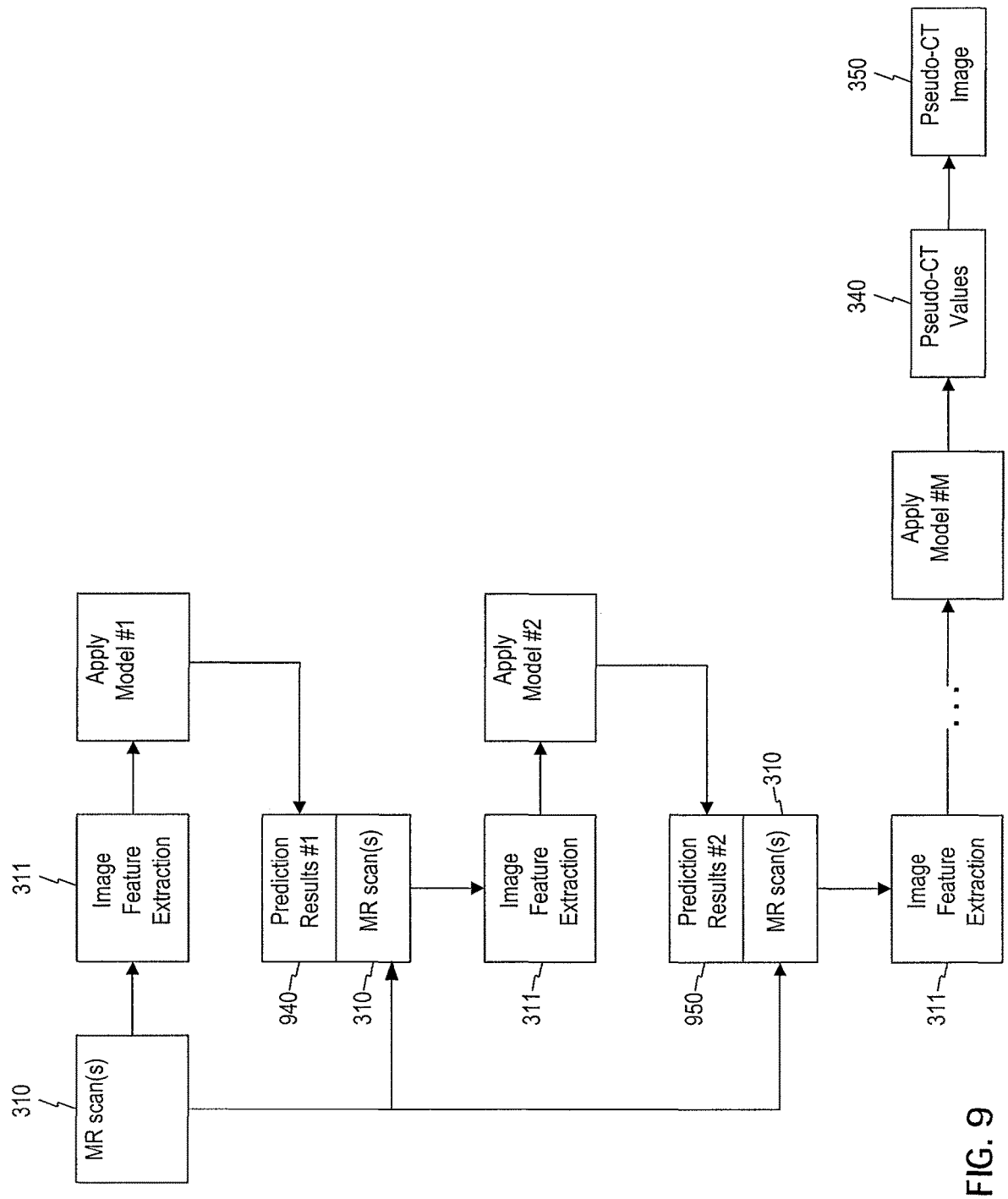
FIG. 9 is a diagram of an exemplary process for using a multi-stage pseudo-CT predictive model to generate a pseudo-CT image.

FIG. 9 illustrates a diagram of an exemplary process for applying multi-stage models to predict pseudo-CT values, consistent with the disclosed embodiments.

As shown in FIG. 9, a processor (e.g., processor 514 shown in FIG. 5) may acquire one or more patients' MR scan(s) 310 from an image acquisition device 440 or from databases 520, 530 (shown in FIG. 5).

Once the patient's MR scan is acquired, a plurality of image features may be extracted for each MR voxel of the MR scan(s). As discussed above with respect to FIG. 2, the extracted image features may include a local pattern feature 212, a landmark feature 214, a context feature 216, and various other types of features 218. The features can be associated with an image point, an image voxel, or an image sample. As shown in FIG. 9, image feature extraction module 311 may be used to extract image features from the MR scan(s). Image features may refer to numerical (e.g., intensity values, coordinate locations of the feature and the like) or categorical properties (e.g., a tissue type, a structure label and the like) of an MR voxel. The extracted image features for each image point may form a feature vector, as discussed above. A set of feature vectors (e.g., 320), for example for all the image points of the MR scan(s) 310 may be input into Model #1 (the model generated in training stage 1 in FIG. 8). In other words, processor 514 may apply Model #1 generated in training stage 1 in the multi-stage training process of FIG. 8 to the set of feature vectors extracted from MR scan 310. Model #1 may output prediction results #1 940 (e.g., pseudo-CT values, segmentation maps, etc., depending on the type of Model #1). Subsequently, prediction results #1 940 and the MR scan(s) 310 may be combined and subjected to another image feature extraction 311. Because more information is provided by prediction results #1 940, more image features may result from the second extraction or the image features result from the second extraction may have better quality than those result from the first extraction. The image features result from the second extraction may form a set of MR feature vectors that can be input into Model #2 generated in training stage 2 of FIG. 8 to generate prediction results #2 950, which may be combined with MR scan(s) 310. Image feature extraction module 311 may again extract a set of MR feature vectors from the combined prediction results #2 950 and MR scan(s) 310. This process is repeated, until the final prediction model Model #M is applied to generate pseudo-CT values 340. According to some embodiments, prediction models Model #1 through Model #M should be applied in the same order as that of the models generated in the training process. The pseudo-CT values 340 may be used to generate pseudo-CT image 350 depicting an accurate visual representation of the patient's anatomical geometry.

In some embodiments, any one of the predictive models Model #1, Model #2, . . . Model #M-1 may be a tissue classification model. For example, Model #1 may be a classification model. Applying Model #1 to feature vectors extracted from MR scan(s) 310 can generate a classification map, such as a tissue classification map. The tissue classification map, along with the MR scan(s) 310 may be used as input to image feature extraction module 311 to generate feature vectors having more information or improved quality, to which Model #2 can be applied. Similar steps can be repeated to further refine the feature vectors. A series of classification models may be provided from the multi-stage training process (FIG. 8). For example, Model #1 may be a classification model A, Model #2 may be a classification model B, and the like. Classification models A and B may be associated with the same tissue class but different refinements, or may be associated with different tissue classes. As discussed above, the final prediction Model #M is a pseudo-CT predictive model that produces pseudo-CT values 340, consistent with the disclosed embodiments.

In some embodiments, the predictive model can be built and trained with training data 110 (shown in FIG. 1) that includes multi-channel MR scans and corresponding CT values. Multi-channel MR scans provide more information than single-channel MR scans. The increased information available with multi-channel MR images allows for more accurate and more robust prediction of CT values to generate a pseudo-CT image. For example, multi-channel MR images allow for conversion from MR intensity values to intrinsic tissue parameter values.

MRI is a highly versatile imaging technique that permits the study of various properties (e.g., both structural and functional) of the human body through the manipulation of magnetic and radio frequency (RF) fields. For standard structural (or anatomical) imaging, the measured MR signal (e.g., MR image intensity) can be a function of a few intrinsic tissue parameters: the proton density (P), the longitudinal relaxation time ($T_1$), and the transverse relaxation time ($T_2$, or $T^*_2$ if considering a magnetic field inhomogeneity effect). For example, for both FLASH and SPGR imaging protocols (e.g., also known as imaging sequences), the MR signal intensity S can be expressed as a function of intrinsic tissue parameters (P, $T_1$, and $T^*_2$) according to Equation 2:

$$S = P\sin\alpha\left(\frac{1 - e^{-TR/T1}}{1 - \cos\alpha e^{-TR/T1}}\right)e^{-TE/T^*_2}, \quad \text{(Equation 2)}$$

where TR, TE, and $\alpha$ are the MR acquisition parameters that the user is free to modify. Different parameters can be used to produce different image contrasts.

In order to predict CT numbers from MR images, a predictive model may rely primarily on the intrinsic tissue parameters (P, $T_1$, and $T^*_2$), instead of the MR signal intensity S that is dependent on sequence parameters (TR, TE, and $\alpha$), because the latter does not, at least directly, represent anatomical properties of the patient.

The use of multi-channel MR images allows the estimation of these intrinsic tissue parameters, because multi-channel MR images can provide a plurality of images with each image having a different setting of the sequence parameters (TR, TE, and a). Therefore, multi-channel MR images allow for the estimation of intrinsic tissue parameters (P, $T_1$, and $T^*_2$) by solving Equation 2 in which multiple values of S and sequence parameters (TR, TE, and $\alpha$) are known. For example, to estimate all three unknown parameters (P, $T_1$, and $T^*_2$), three MR images (e.g., three channels) are needed. Using additional channels would improve the robustness of the parameter estimation by reducing image noise.

Figure 11:
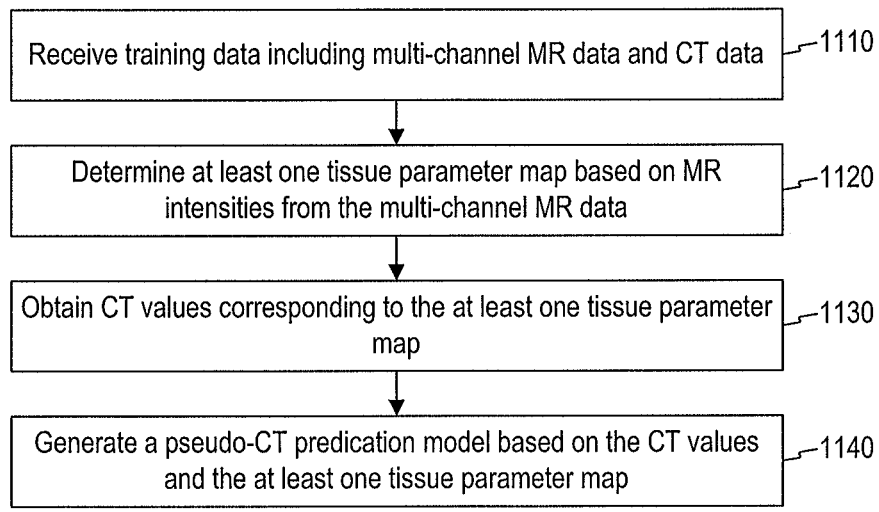
FIG. 11 is a flow chart of an exemplary method of building a pseudo-CT predictive model using multi-channel MR data.
Figure 12:
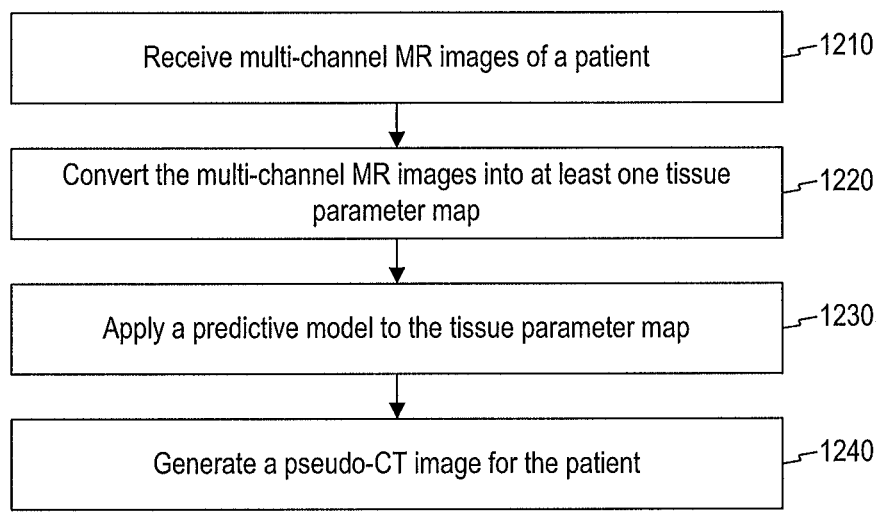
FIG. 12 is a flowchart of an example method for generating a pseudo-CT image for a patient using multi-channel MR images.

In some embodiments, the workflow for implementing the disclosed method includes two stages: training (e.g., model construction) stage and application (e.g., pseudo-CT generation) stage. In some embodiments, the training stage only needs to be computed once after the training data are collected. After the prediction model is trained, in the application stage, the trained model can be applied to new multi-channel MR scans to create a pseudo-CT image for a new patient with only multi-channel MR scans. In the following description, FIGS. 10 and 11 are directed to the training stage, while FIG. 12 is directed to the prediction stage.

Figure 10:
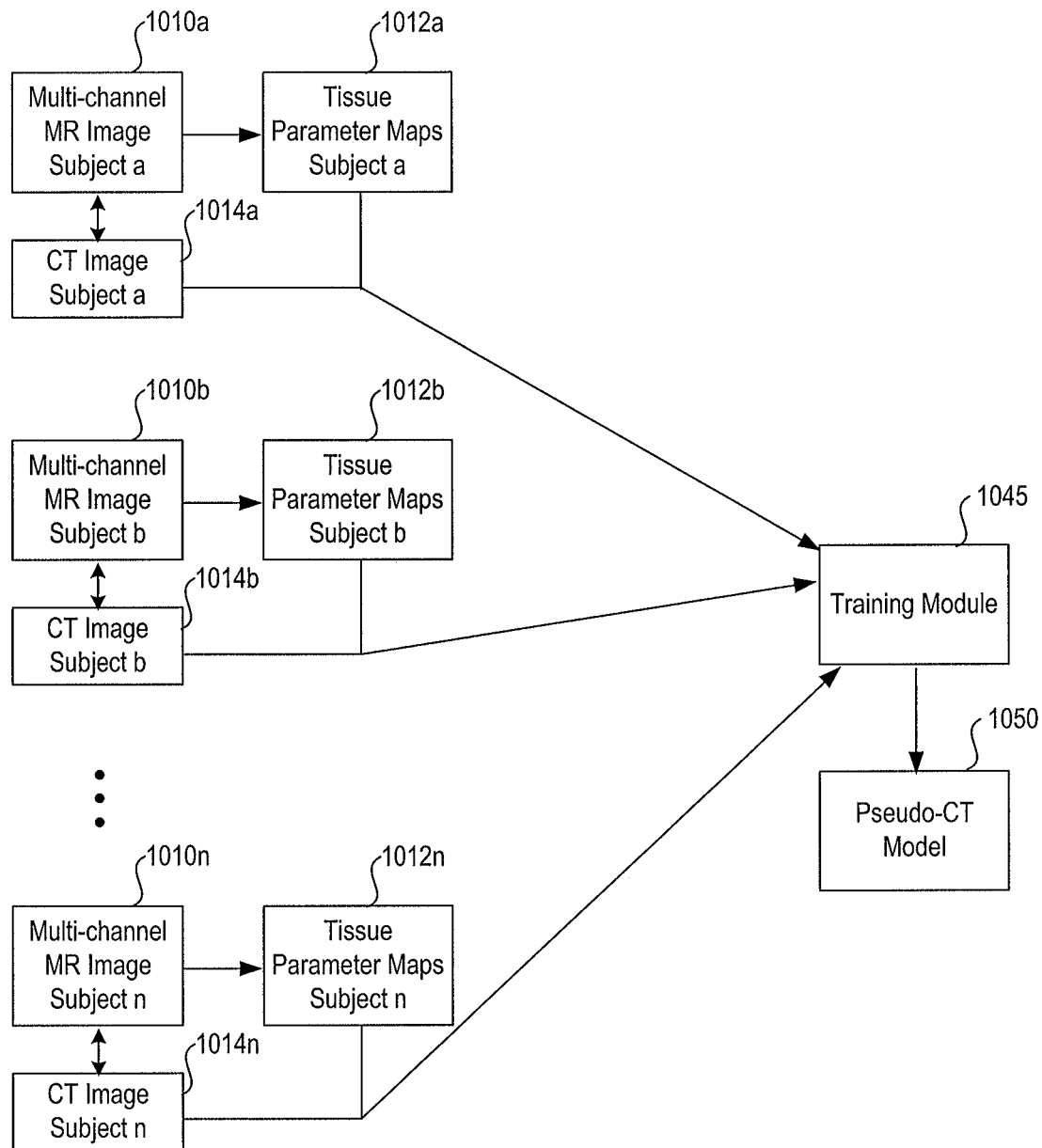
FIG. 10 is a diagram of an exemplary process for training a pseudo-CT predictive model using tissue parameter estimated from multi-channel MR scans.

FIG. 10 illustrates a diagram of an exemplary process for training a pseudo-CT predictive model using tissue parameters estimated from multi-channel MR scans. Similar to the process shown in FIG. 1, training data from a plurality of training subjects having both CT scans and multi-channel MR scans can be collected. For example, as shown in FIG. 10, multi-channel MR image data 1010a and CT image data 1014a can be collected for subject a. Multi-channel MR data 1010a may include a plurality of MR images obtained using different sequence parameter sets. Similarly, multi-channel MR image data 1010b and CT image data 1014b can be acquired for subject b. The multi-channel MR image data and CT image data can be collected from image acquisition device (e.g., 440) or from image database (e.g., 520, 530). The process of data acquisition/collection goes on until the nth set of data (e.g., 1010n and 1014n) has been included in the training data. In one embodiment, the training data shown in FIG. 10 are similar to training data 110 in FIG. 1 except that the MR image data in FIG. 10 are multi-channel MR data while the MR data in FIG. 1 can be either single-channel or multi-channel MR data.

In some embodiments, the CT scans (e.g., 1014a) and multi-channel MR scans (e.g., 1010a) are aligned. If not, auto- or semi-automated image registration or alignment procedure can be applied to align them. As described above, an aligned pair of CT image and MR image means that for each voxel (e.g., indicating a spatial location of the image) the corresponding CT and MR image values are known or the correspondence relationship is known. In addition, MR images may also undergo some procedure for correcting geometric distortions.

The present application discloses a learning-based approach to build and train a prediction model using training data. In an embodiment, the prediction model can be a regression model or a regression function as the output of the prediction model can be a continuous variable (e.g., a CT value).

Many statistical or machine learning methods can be used to build and/or train a prediction model that can predict the CT image intensities (also known as CT values or CT numbers) based on features derived from the MR images. For example, supervised learning is a branch of machine learning that can be used to determine a prediction model based on a set of training data. Each sample of the training data is a pair including input data (e.g., a vector of measurements or features) and a desired output value (e.g., a supervisory signal). A supervised learning algorithm can analyze the training data and produce a predictor function (e.g., a regression function) when the output variable is numeric or continuous, which is usually true in the application of generating pseudo-CT images. Various algorithms can be applied to determine the prediction model, including but not limited to: support vector machines, neural networks, decision trees, and random forests.

The predictive model, once trained using the training data, can be used to generate pseudo-CT images for any new set of multi-channel MR scans of the same or a different patient.

Embodiments of the present application may convert MR intensity values (e.g., S) to intrinsic tissue parameters (e.g., P, $T_1$, $T^*_2$, or $T^*_2$) and construct the prediction model based on intrinsic tissue parameters. As discussed above, the ability to use MR imaging provides greater flexibility and less radiation exposure over CT imaging but the MR intensity values cannot be directly used in dosage calculation because they are sequence dependent. Training the predictive model using the intrinsic tissue parameters instead of using raw MR intensity values may provide a predictive model that is sequence independent. Being sequence independent can be advantageous because the imaging sequences or sequence parameters are easily modifiable and often vary significantly among different clinics. By designing the predictive model to be sequence independent, data acquired from different MR scanners, different MR imaging sequences, or different clinics can be used together, provided that the MR sequences can be used to estimate intrinsic tissue parameters. In addition, the MR imaging sequences for new patients do not need to be the same as the MR imaging sequences used by the training data. Therefore, a user can freely design new MR imaging sequences for future patients without the need to acquire new training data to train the predictive model.

To build a prediction model based on tissue parameters, the MR image intensities need to be converted into tissue parameter values for each patient. This can be achieved by solving an MR imaging equation (e.g., Equation 2) at every image point (e.g., voxel) of the patient's MR images. A set of tissue parameter images (also referred to as tissue parameter maps) can be produced. The set may include one tissue parameter map for each of the tissue parameters. For example, the set may include a map of P, a map of $T_1$, and a map of $T_2$ or $T^*_2$. The tissue parameter values are intrinsic values reflecting the properties of the underlying tissue or organ of the patient's body. Further, because the CT image is aligned with the MR images for each training subject, the CT image is further aligned with the tissue parameter maps generated from the MR images.

As shown in FIG. 10, tissue parameter maps for each training subject may be generated based on multi-channel MR image data. For example, tissue parameter maps 1012a of subject a may include a set of all three tissue parameter maps. In some embodiments, if estimation of all tissue parameters from multi-channel MR images is difficult, a model can also be built using only a subset of the tissue parameters. Once tissue parameter maps of each training subject are obtained (e.g., 1012b, . . . , 1012n), tissue parameter maps may be used together with the corresponding CT image to build and train a pseudo-CT prediction model 1050 using a training module 1045 (e.g., using statistical or machine learning techniques). In some embodiments, for each image point (e.g., voxel), the set of tissue parameters may be treated as features included in the feature vector as described in FIG. 1. For example, if all three tissue parameters are used, a feature vector of [P, $T_1$, $T^*_2$] may be constructed. This tissue parameter feature vector may be used alone or in combination with other features as discussed in connection with FIG. 2 for building and training a predictive model. The disclosed techniques of building and training predictive model 150 discussed above are also applicable to the process of building and training predictive model 1050.

FIG. 11 is a flow chart of an exemplary method 1100 of building a pseudo-CT predictive model using multi-channel MR data. Method 1100 may be implemented by system 500. At step 1110, processor 514 may receive training data including multi-channel MR data (e.g., 1010a, 1010b, etc.) and CT data (e.g., 1014a, 1014b, etc.). The multi-channel MR data may include multi-channel MR images for one or more patients. In some embodiments, the multi-channel MR data may include at least two multi-channel MR images for each patient. Multi-channel MR images of the same patient may be obtained using different imaging sequence parameters. The CT data may include CT images for one or more patients. In some embodiments, the CT data may include at least one CT image for each patient. If multiple CT images are available, they can be averaged to reduce image noise. For a given patient, the CT image and the multi-channel MR images may be aligned. In some embodiments, if the CT image and the multi-channel MR images are not aligned, image registration techniques may be used to align them.

At step 1120, processor 514 may determine at least one tissue parameter map (e.g., 1012a, 1012b, etc.) based on MR intensities from the multi-channel MR data. For example, at least one tissue parameter map of P, $T_1$, or $T^*_2$ may be estimated using MR intensity values of multiple MR images of a patient by solving Equation 2. Because Equation 2 is a nonlinear equation, fitting techniques can be used to estimate tissue parameter values based on multiple sets of MR intensities (S) and sequence parameters (TR, TE, and α), which are known based on the multi-channel MR data. As described above, all three tissue parameter maps are preferred, but a subset of the tissue parameter maps may also be used.

In some embodiments, a tissue parameter map may be generated by estimating individual image points. For example, a set of tissue parameter values including several kinds of tissue parameters (e.g., P, $T_1$, $T^*_2$ or $T^*_2$) may be estimated at every image point. The corresponding tissue parameter map can then be formed as a collection of all tissue parameter values of a particular kind.

At step 1130, processor 514 may obtain CT values corresponding to the tissue parameter map(s) generated at step 1120. In some embodiments, the CT values may be the CT intensity values of the CT image for the same patient as the tissue parameter map(s). As described above, because the CT image is aligned with the MR images, the CT image is also aligned with the tissue parameter map(s) converted from the MR images.

At step 1140, processor 514 may generate a pseudo-CT prediction model (e.g., 1050) based on the CT values and the tissue parameter map(s). In some embodiments, the CT values and the tissue parameter map(s) may be input to a training module (e.g., 1045) to train the pseudo-CT model 1050. Regression methods such as statistical learning or machine learning techniques may be used by training module 1045 to train the predictive model. The trained predictive model 1050 may be a mathematical or statistical model that can be used to predict a CT number based on one or more tissue parameter values (e.g., P, $T_1$, $T^*_2$, $T^*_2$). As described above, while it is preferable to use all tissue parameters, a model can also be built using only a subset of the tissue parameters.

FIG. 12 is a flowchart of an example method 1200 for generating a pseudo-CT image for a patient using multi-channel MR images. Method 1200 may be implemented by system 500 and used to generate pseudo-CT images for a new patient using the predictive model (e.g., 1050) built by method 1100.

At step 1210, processor 514 may receive multi-channel MR images of a patient (e.g., a new patient) from, for example, image acquisition device 440 or database 520, 530. The received multi-channel MR images may not have corresponding CT images. At step 1220, processor 514 may convert the multi-channel MR images into at least one tissue parameter map. For example, processor 514 may convert the multi-channel MR images into tissue parameter map(s) by solving Equation 2 using fitting technique or the like. One or more tissue parameter maps, such as maps of P, $T_1$, $T^*_2$, and/or $T^*_2$, may be generated by the conversion process 1220. As described above, while it is preferable to have all tissue parameter maps, in some embodiments a subset of the maps may also be used.

At step 1230, processor 514 may apply a predictive model (e.g., 1050) to the tissue parameter map(s). For example, the converted tissue parameter map(s) may be used as input to the predictive model. In some embodiments, the predictive model may operate in a point-wise manner, in which the predictive model predicts the CT number at each location of the patient image (e.g., pseudo-CT image) based on tissue parameter value(s) computed at that location. More complex prediction models may also be used. For example, a model can take into account of nearby tissue parameter value(s) for each point, which can improve robustness with respect to data noise. A model may also make prediction based on a combination of the tissue parameter value(s) and other information such as the image point location or other features that can be derived from the tissue parameter map(s)—e.g., texture, gradient, etc.

At step 1240, a pseudo-CT image for the patient may be generated by assembling the pseudo-CT values resulting from step 1230.

To train a predictive model and to use the model to predict the pseudo-CT values, parametric methods such as linear regression or ordinary least squares regression may be used. In these parametric methods, the regression function is defined in terms of a finite number of unknown model parameters that can be estimated from input data. For example, a regression model can be defined as:

$$H \approx f(X, \beta),$$

where H denotes the CT values to be predicted, X denotes a vector of input variables, e.g., tissue parameter values (P, $T_1$, and $T^*_2$ (or $T_2$)), and β denotes a vector of unknown model parameters for the regression model. One exemplary model is a linear regression model defined as:

$$H \approx \beta_1 P + \beta_2 T_1 + \beta_3 T^*_2$$

In the training stage, training data can provide a large number of observations, for example, a set of known H values (e.g., provided by CT scans at step 1130) with corresponding P, $T_1$, and $T^*_2$ values (e.g., provided by converting MR scans at step 1120). Using these observation data, model parameters β can then be computed or trained (e.g., using least square fitting). Once β is obtained after training, the model can then be used to compute H for a new set of P, $T_1$, and $T^*_2$ values (e.g., in the prediction stage using method 1200).

In some embodiments, instead of or in addition to using the tissue parameters as the input data for the prediction model, other information can also be collected. For example, extra features that can be computed or collected include but not limited to:

- The coordinates of an image point, or normalized coordinates with respect to an external reference space or to one or a few internal landmark points;
- Curvatures of the tissue parameter map(s) computed at a sample point location;
- Texture measures of the tissue parameter map(s) computed at a sample point location; and
- Patches of local tissue parameter values, e.g., tissue parameter values within a 5×5×5 neighborhood of a sample point.

Computer programs based on the written description and methods of this specification are within the skill of a software developer. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. It is intended, therefore, that the specification and examples be considered as example only, with a true scope and spirit being indicated by the following claims and their full scope of equivalents.

What is claimed is:

1. A system comprising:
   processing circuitry; and
   a storage device communicatively coupled to the processing circuitry, the storage device storing instructions that, when executed by the processing circuitry, configures the processing circuitry to perform operations comprising:
      receiving a first Magnetic Resonance (MR) image of a subject;
      extracting a feature from the first MR image of the subject; and
      generating, based on a machine learning technique, a pseudo-CT image from the extracted feature of the first MR image, wherein the machine learning technique has been trained to model a relationship between a Computerized Tomography (CT) value parameter H, a tissue value parameter, and a β parameter based at least in part on:
         extracting a plurality of features from a plurality of image points of a plurality of Magnetic Resonance (MR) images associated with a plurality of training subjects;
         receiving a plurality of CT images associated with the plurality of training subjects;
         averaging values for the plurality of training subjects associated with the plurality of CT images;
         storing the plurality of extracted features in a respective dimension of a plurality of dimensions of a feature vector for an image point of the plurality of image points;
         extracting a CT value for an image point of the plurality of image points of a CT image of the plurality of CT images;
         aligning a given MR image of the plurality of MR images and the CT image;
         denoting the CT value parameter H to be the extracted CT value and the tissue value parameter to be the feature vector; and
         performing a data fitting technique on the denoted CT value parameter H and the tissue value parameter to compute the β parameter, such that the CT value parameter H is represented by a mathematical combination of the β parameter and the tissue value parameter, wherein the pseudo-CT image is generated as a function of the β parameter and the extracted feature of the first MR image.

2. The system of claim 1, wherein the operations further comprise accessing a database to retrieve training data including at least one MR image of the plurality of MR images and at least one CT image of the plurality of CT images for the plurality of training subjects.

3. The system of claim 2, wherein the training data include multiple CT images for at least one of the plurality of training subjects.

4. The system of claim 2, wherein the given MR image and the CT image correspond to a first of the plurality of training subjects.

5. The system of claim 1, wherein the relationship modeled by the machine learning technique corresponds to:

$$H \approx \beta_1 P + \beta_2 T_1 + \beta_3 T^*_2,$$

wherein H corresponds to the CT value parameter H, $\beta_1$, $\beta_2$, $\beta_3$ correspond to the β parameter, and P, $T_1$, $T^*_2$ correspond to the tissue value parameter.

6. The system of claim 1, wherein the operations further comprise:
   reducing the dimensions of the feature vector; and
   generating the pseudo-CT image based on the feature vector having the reduced dimensions and CT values of a plurality of training subjects.

7. The system of claim 6, wherein reducing the dimensions of the feature vector comprises reducing noise or redundancy in the feature vectors.

8. The system of claim 6, wherein reducing the dimensions of the feature vectors comprises removing signals irrelevant to the CT image.

9. The system of claim 1, wherein the extracted features include at least one of local pattern feature, landmark feature, or context feature.

10. The system of claim 1, wherein the operations further comprising:
    for each of the plurality of training subjects:
       extracting features from a given image point of the given MR image;
       storing the extracted features in the respective dimension of the plurality of dimensions of the feature vector for the given image point;
       extracting a given CT value for the image point of a given CT image; and
       aligning the given MR image and the given CT image.

11. A method comprising:
    receiving, by processing circuitry, a first Magnetic Resonance (MR) image of a subject;
    extracting, by the processing circuitry, a feature from the first MR image of the subject; and
    generating, by the processing circuitry, based on a machine learning technique, a pseudo-CT image from the extracted feature of the first MR image, wherein the machine learning technique has been trained to model a relationship between a Computerized Tomography (CT) value parameter H, a tissue value parameter, and a β parameter based at least in part on:
       extracting a plurality of features from a plurality of image points of a plurality of Magnetic Resonance (MR) images associated with a plurality of training subjects;
       receiving a plurality of CT images associated with the plurality of training subjects;
       averaging values for the plurality of training subjects associated with the plurality of CT images;

storing the plurality of extracted features in a respective dimension of a plurality of dimensions of a feature vector for an image point of the plurality of image points;

extracting a CT value for an image point of the plurality of image points of a CT image of the plurality of CT images;

aligning a given MR image of the plurality of MR images and the CT image;

denoting the CT value parameter H to be the extracted CT value and the tissue value parameter to be the feature vector; and performing a data fitting technique on the denoted CT value parameter H and the tissue value parameter to compute the β parameter, such that the CT value parameter H is represented by a mathematical combination of the β parameter and the tissue value parameter, wherein the pseudo-CT image is generated as a function of the β parameter and the extracted feature of the first MR image.

12. The method of claim 11 further comprising accessing a database to retrieve training data including at least one MR image of the plurality of MR images and at least one CT image of the plurality of CT images for the plurality of training subjects.

13. The method of claim 12, wherein the training data include multiple CT images for at least one of the plurality of training subjects.

14. The method of claim 12, wherein the given MR image and the CT image correspond to a first of the plurality of training subjects.

15. The method of claim 11, wherein the relationship modeled by the machine learning technique corresponds to:

$$H \approx \beta_1 P + \beta_2 T_1 + \beta_3 T^*_2,$$

wherein H corresponds to the CT value parameter H, $\beta_1$, $\beta_2$, $\beta_3$ correspond to the β parameter, and P, $T_1$, $T^*_2$ correspond to the tissue value parameter.

16. The method of claim 11 further comprising:
reducing the dimensions of the feature vector; and
generating the pseudo-CT image based on the feature vector having the reduced dimensions and CT values of the plurality of training subjects.

17. The method of claim 16, wherein reducing the dimensions of the feature vector comprises reducing noise or redundancy in the feature vectors.

18. The method of claim 16, wherein reducing the dimensions of the feature vectors comprises removing signals irrelevant to the CT image.

19. The method of claim 11, wherein the extracted features include at least one of local pattern feature, landmark feature, or context feature.

20. A non-transitory computer readable medium comprising non-transitory computer readable instructions for instructing processing circuitry to perform operations comprising:

receiving a first Magnetic Resonance (MR) image of a subject;

extracting a feature from the first MR image of the subject; and generating, based on a machine learning technique, a pseudo-CT image from the extracted feature of the first MR image, wherein the machine learning technique has been trained to model a relationship between a Computerized Tomography (CT) value parameter H, a tissue value parameter, and a β parameter based at least in part on:

extracting a plurality of features from a plurality of image points of a plurality of Magnetic Resonance (MR) images associated with a plurality of training subjects;

receiving a plurality of CT images associated with the plurality of training subjects;

averaging values for the plurality of training subjects associated with the plurality of CT images;

storing the plurality of extracted features in a respective dimension of a plurality of dimensions of a feature vector for an image point of the plurality of image points;

extracting a CT value for an image point of the plurality of image points of a CT image of the plurality of CT images;

aligning a given MR image of the plurality of MR images and the CT image;

denoting the CT value parameter H to be the extracted CT value and the tissue value parameter to be the feature vector; and performing a data fitting technique on the denoted CT value parameter H and the tissue value parameter to compute the β parameter, such that the CT value parameter H is represented by a mathematical combination of the β parameter and the tissue value parameter, wherein the pseudo-CT image is generated as a function of the β parameter and the extracted feature of the first MR image.

* * * * *